United States Patent
Hresko et al.

(10) Patent No.: US 11,508,474 B2
(45) Date of Patent: Nov. 22, 2022

(54) EVENT RECONSTRUCTION FOR A MEDICAL DEVICE

(71) Applicant: Zoll Medical Corporation, Chelmsford, MA (US)

(72) Inventors: Patrick Hresko, Mount Pleasant, PA (US); Marc C. Brenner, Aspinwall, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 217 days.

(21) Appl. No.: 15/472,908

(22) Filed: Mar. 29, 2017

(65) Prior Publication Data

US 2017/0300653 A1    Oct. 19, 2017

Related U.S. Application Data

(60) Provisional application No. 62/316,139, filed on Mar. 31, 2016.

(51) Int. Cl.
| | |
|---|---|
| *G16H 10/20* | (2018.01) |
| *G16H 40/60* | (2018.01) |
| G16H 15/00 | (2018.01) |
| G16H 20/30 | (2018.01) |

(52) U.S. Cl.
CPC ............ *G16H 40/60* (2018.01); *G16H 10/20* (2018.01); *G16H 15/00* (2018.01); *G16H 20/30* (2018.01)

(58) Field of Classification Search
CPC ................ G06F 19/30; G06K 9/00496; G06Q 50/22–24
See application file for complete search history.

(56) References Cited

U.S. PATENT DOCUMENTS

| | | | |
|---|---|---|---|
| 5,078,134 A | 1/1992 | Heilman et al. | |
| 6,681,003 B2 | 1/2004 | Linder et al. | |
| 7,805,191 B2 | 9/2010 | Walker et al. | |
| 8,271,082 B2 | 9/2012 | Donnelly et al. | |
| 8,639,348 B2 | 1/2014 | Geheb | |
| 8,768,441 B2 * | 7/2014 | De Zwart | G06F 19/3418 600/510 |
| 8,781,751 B2 * | 7/2014 | Kouchi | A61B 5/044 702/19 |
| 9,730,648 B2 * | 8/2017 | Kassem | A61B 5/743 |

(Continued)

*Primary Examiner* — Jonathan Ng
(74) *Attorney, Agent, or Firm* — The Webb Law Firm

(57) ABSTRACT

A device for graphically reconstructing information received from a medical device is provided. The device comprises an event processor configured to process information received from a medical device by receiving electrocardiogram (ECG) recordings and determining at least one cardiac event based on the ECG recordings, receiving data corresponding to non-cardiac event(s), determining a time of occurrence or a time period associated with the cardiac event(s), determining times of occurrences and time periods associated with the non-cardiac event(s), correlating the time of occurrence or time period associated with the cardiac event(s) and the non-cardiac event(s), identifying one or more gaps in the ECG recordings, and reconstructing the ECG recordings during the one or more gaps based at least in part on the received non-cardiac data. The event processor is also configured to generate a graphical representation of the processed information based on the cardiac event(s) and non-cardiac event(s).

18 Claims, 10 Drawing Sheets

(56) References Cited

U.S. PATENT DOCUMENTS

| | | | |
|---|---|---|---|
| 2009/0156908 A1* | 6/2009 | Belalcazar | A61B 5/287 |
| | | | 600/301 |
| 2011/0295078 A1 | 12/2011 | Reid et al. | |
| 2013/0096649 A1 | 4/2013 | Martin et al. | |
| 2013/0124090 A1 | 5/2013 | Gotschall et al. | |
| 2013/0296719 A1 | 11/2013 | Packer et al. | |
| 2013/0324868 A1* | 12/2013 | Kaib | A61B 5/48 |
| | | | 600/510 |
| 2014/0047314 A1 | 2/2014 | Esibov et al. | |
| 2014/0201627 A1 | 7/2014 | Freeman et al. | |
| 2014/0342330 A1 | 11/2014 | Freeman et al. | |
| 2016/0192853 A1* | 7/2016 | Bardy | A61B 5/333 |
| | | | 600/382 |
| 2016/0228069 A1* | 8/2016 | Derkx | A61B 5/113 |
| 2016/0345854 A1* | 12/2016 | Bardy | A61B 5/02405 |
| 2019/0341135 A1* | 11/2019 | Whiting | A61B 5/0015 |

* cited by examiner

EVENT RECONSTRUCTION FOR A MEDICAL DEVICE

CROSS REFERENCE TO RELATED APPLICATION

This application claims priority to U.S. Provisional Patent Application No. 62/316,139 filed Mar. 31, 2016, entitled "Event Reconstruction for a Medical Device", the disclosure of which is hereby incorporated in its entirety by reference.

BACKGROUND

Technical Field

The present disclosure relates to devices and methods for displaying information from a medical device worn by a patient.

Description of Related Art

There are a wide variety of electronic and mechanical devices for monitoring and treating patients' medical conditions. In some examples, depending on the underlying medical condition being monitored or treated, medical devices such as cardiac pacemakers or defibrillators, may be surgically implanted or connected externally to the patient.

One of the most deadly cardiac arrhythmias is ventricular fibrillation, which occurs when a heart's normal, regular electrical impulses are replaced by irregular and rapid impulses, causing the heart to stop normal contractions and to begin to quiver. Normal blood flow ceases, and organ damage or death can result within minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

More specifically, such devices are configured to continuously or substantially continuously monitor the patient's heart for treatable arrhythmias and, when an arrhythmia is detected, to apply corrective electrical pulses directly to the heart. Wearable pacing devices and/or defibrillators have been developed for a certain population of patients, e.g., those who have recently experienced a heart attack and/or who are susceptible to heart arrhythmias, as well as patients who are awaiting an implantable device.

During continuous or substantially continuous monitoring of the patient, recordings including information about the patient and device are obtained from a number of different types of sensors. The obtained information can be analyzed by the device and stored on an associated computer-readable memory. Portions of the information can be sent from the medical device to remote servers or computer workstations for review by a service technician or data reviewer. The data reviewer can also prepare patient reports for a patient's physician and/or caregiver based on the received information. In currently available systems, such information is presented to a reviewer in a disparate manner. Improved devices and methods for displaying such disparate data in a coordinated and interactive manner are needed. The present disclosure is directed to methods and systems for graphically representing information received from a medical device in such a manner.

SUMMARY

According to an aspect of the disclosure, a device for graphically reconstructing information received from a medical device worn by a patient is provided. The device comprises: an event processor configured to: process information received from a medical device by receiving one or more electrocardiogram (ECG) recordings over a time interval and determining at least one cardiac event during the time interval based on the one or more ECG recordings, receiving data over the time interval corresponding to one or more non-cardiac events, determining at least one of a time of occurrence and a time period associated with the at least one cardiac event, determining at least one of times of occurrences and time periods associated with the one or more non-cardiac events, correlating the at least one of a time of occurrence and a time period associated with the at least one cardiac event and the at least one of times of occurrences and time periods associated with the one or more non-cardiac events, identifying one or more gaps in the ECG recordings during the time interval, and reconstructing the ECG recordings during the one or more gaps based at least in part on the non-cardiac data received during the time interval. The event processor is also configured to generate a graphical representation of the processed information based on the at least one cardiac event and the one or more non-cardiac events. The device further comprises an output device operably connected to the event processor and configured to display the graphical representation of the processed information.

According to another aspect of the disclosure, a computer-implemented method for graphically reconstructing information received from a medical device worn by a patient is illustrated. The method comprises: processing information received from the medical device by receiving one or more ECG recordings over a time interval from the medical device, determining at least one cardiac event during the time interval based on the one or more ECG recordings, receiving data over the time interval corresponding to one or more non-cardiac events, determining at least one of a time of occurrence and a time period associated with the at least one cardiac event, determining at least one of times of occurrences and time periods associated with the one or more non-cardiac events, correlating the at least one of a time of occurrence and a time period associated with the at least one cardiac event and the at least one of times of occurrences and time periods associated with the one or more non-cardiac events, identifying one or more gaps in the ECG recordings during the time interval, and reconstructing the ECG recordings during the one or more gaps based at least in part on the non-cardiac data received during the time interval. The method further comprises generating a graphical representation of the processed information based on the at least one cardiac event and the one or more non-cardiac events; and causing an output device to display the graphical representation of the information.

According to another aspect of the disclosure, a device for providing dynamic viewing of information received from a medical device worn by a patient is provided. The device comprises: an event processor configured to process information received from a medical device by receiving one or more ECG recordings over a time interval, receiving data over the time interval corresponding to one or more non-cardiac events, identifying one or more gaps in the ECG recordings during the time interval, and reconstructing the ECG recordings during the one or more gaps based at least in part on the non-cardiac data received during the time interval. The event processor is further configured to generate a graphical representation of the processed information. The device further comprises at least one user interface configured to be displayed on an output device operably connected to the event processor. The at least one user interface is configured to display the graphical representation of the processed information, and a slider configured to be manipulated by a user, the slider defining at least one time or range of times within the time interval, wherein manipulation of the slider changes the time or range of times of the displayed graphical representation.

Non-limiting aspects or embodiments of the present disclosure will now be described in the following numbered clauses:

Clause 1: A device for graphically reconstructing information received from a medical device worn by a patient is provided. The device comprises: an event processor configured to process information received from a medical device by receiving one or more ECG recordings over a time interval and determining at least one cardiac event during the time interval based on the one or more ECG recordings, receiving data over the time interval corresponding to one or more non-cardiac events, determining at least one of a time of occurrence and a time period associated with the at least one cardiac event, determining at least one of times of occurrences and time periods associated with the one or more non-cardiac events, correlating the at least one of a time of occurrence and a time period associated with the at least one cardiac event and the at least one of times of occurrences and time periods associated with the one or more non-cardiac events, identifying one or more gaps in the ECG recordings during the time interval, reconstructing the ECG recordings during the one or more gaps based at least in part on the non-cardiac data received during the time interval, and generating a graphical representation of the processed information based on the at least one cardiac event and the one or more non-cardiac events; and an output device operably connected to the event processor and configured to display the graphical representation of the processed information.

Clause 2. The device of clause 1, wherein the graphical representation comprises at least one of an event timeline, a histogram, and a three-dimensional chart based on the at least one cardiac event and the one or more non-cardiac events.

Clause 3. The device of clause 1 or clause 2, wherein the graphical representation comprises an event timeline, the event timeline including, at least in part, a time-dependent waveform generated from the one or more ECG recordings.

Clause 4. The device of any of clauses 1-3, wherein the at least one cardiac event comprises an event associated with at least one ECG recording.

Clause 5. The device of any of clauses 1-3, wherein the at least one cardiac event comprises one or more of: a patient-initiated event, a remotely triggered event, a device-initiated event, and a cardiac arrhythmia event, and wherein the graphical representation comprises an indication of event type.

Clause 6. The device of any of clauses 1-5, wherein the one or more non-cardiac events comprises an electrode noise event and the graphical representation provides a reviewer with an ability to determine a potential cause of the electrode noise event.

Clause 7. The device of any of clauses 1-5, wherein the one or more non-cardiac events comprises an electrode fall-off event and the graphical representation provides the reviewer with an ability to determine a potential cause of the electrode fall-off event.

Clause 8. The device of any of clauses 1-7, wherein the at least one cardiac event comprises a false alarm to the patient and the graphical representation provides a reviewer with an ability to determine a potential cause of the false alarm.

Clause 9. The device of clause 8, wherein the graphical representation provides the reviewer with an ability to review information about the one or more non-cardiac events with respect to the at least one of the time of occurrence and the time period associated with the false alarm to determine the potential cause of the false alarm.

Clause 10. The device of any of clauses 1-10, wherein the graphical representation provides the reviewer with an ability to review information about one or more of a system, subsystem, and a component of the medical device during analysis of the at least one cardiac event.

Clause 11. The device of clause 10, wherein the information about the one or more of the system, subsystem, and a component of the medical device includes battery information, electrode status information, and controller status information.

Clause 12. The device of any of clauses 1-11, wherein the one or more non-cardiac events comprises one or more of a non-cardiac physiological event, a device-initiated non-cardiac event, an event related to a patient physical activity, and an event related to a patient location.

Clause 13. The device of any of clauses 1-12, wherein the data from the medical device for determining the non-cardiac event comprises information received from one or more of a motion sensor, a pressure sensor, a heart rate monitor, a heart audio sensor, a blood pressure sensor, a pulse oximetry sensor, a single axis accelerometer, a multi-axis accelerometer, a gyroscope, and/or manually entered patient survey results.

Clause 14. The device of any of clauses 1-13, further comprising information relating to patient physical activity, the information relating to patient activity comprises an indication of one or more of: patient body position, patient body angle, type of activity being performing by the patient, time performing the activity, movement speed, and/or movement rate.

Clause 15. The device of clause 14, wherein the indication of patient activity further comprises a visual indicator of a patient action, the action comprising one of laying down, sitting, standing, walking, or running.

Clause 16. The device of clause 12, wherein the graphical representation of the information based on a device-initiated event comprises an indication of one or more of: a number of device faults over the time interval, a time and duration of device faults over the time interval, an amount of time since the most recent fault, a device battery level, a number of electrode fall off events over the time interval, pulse voltage information, pulse current information, a number of abnormal device shutdowns over the time interval, diagnostic test results, and/or electrode noise information.

Clause 17. The device of clause 16, wherein the indication of the device-initiated event comprises an icon, and wherein at least a portion of the icon has a first appearance when the device is operating normally and at least a portion of the icon has a second appearance when an anomaly is detected.

Clause 18. The device of clause 1, wherein the graphical representation of the information further comprises at least one overall metric calculated from the information from the medical device over the time interval, the overall metric comprising one or more of a number of treatments administered by a medical device over the interval, an amount of time with substantially normal cardiac activity over the time interval, an amount of time with abnormal cardiac activity over the time interval, an amount of time in which the received information include signal noise above a threshold amount, a patient active time over the time interval, a device wear time over the predetermined time interval, a number of identified device faults over the time interval, and/or a number of identified signal noise events over the time interval.

Clause 19. A computer-implemented method for graphically reconstructing information received from a medical device worn by a patient is provided. The method comprises: processing information received from the medical device by receiving one or more ECG recordings over a time interval from the medical device, determining at least one cardiac event during the time interval based on the one or more ECG recordings, receiving data over the time interval corresponding to one or more non-cardiac events, determining at least one of a time of occurrence and a time period associated with the at least one cardiac event, determining at least one of times of occurrences and time periods associated with the one or more non-cardiac events, correlating the at least one of a time of occurrence and a time period associated with the at least one cardiac event and the at least one of times of occurrences and time periods associated with the one or more non-cardiac events, identifying one or more gaps in the ECG recordings during the time interval, and reconstructing the ECG recordings during the one or more gaps based at least in part on the non-cardiac data received during the time interval; generating a graphical representation of the processed information based on the at least one cardiac event and the one or more non-cardiac events; and causing an output device to display the graphical representation of the information.

Clause 20. The method of clause 19, wherein the graphical representation comprises at least one of an event timeline, a histogram, and a three-dimensional chart based on the at least one cardiac event and the one or more non-cardiac events.

Clause 21. The method of clause 19, wherein the graphical representation comprises an event timeline, the event timeline including, at least in part, a time-dependent waveform generated from the one or more ECG recordings.

Clause 22. The method of any of clauses 19-21, wherein the at least one cardiac event comprises an electrode noise event and the graphical representation provides a reviewer with an ability to determine a potential cause of the electrode noise event.

Clause 23. The method of any of clauses 19-21, wherein the at least one cardiac event comprises a false alarm to the patient and the graphical representation provides a reviewer with an ability to determine a potential cause of the false alarm.

Clause 24. A device for providing dynamic viewing of information received from a medical device worn by a patient is provided. The device comprises: an event processor configured to process information received from a medical device by receiving one or more ECG recordings over a time interval, receiving data over the time interval corresponding to one or more non-cardiac events, identifying one or more gaps in the ECG recordings during the time interval, reconstructing the ECG recordings during the one or more gaps based at least in part on the non-cardiac data received during the time interval, and generating a graphical representation of the processed information; and at least one user interface configured to be displayed on an output device operably connected to the event processor, the at least one user interface displaying the graphical representation of the processed information, and a slider configured to be manipulated by a user, the slider defining at least one time or range of times within the time interval, wherein manipulation of the slider changes the time or range of times of the displayed graphical representation.

Clause 25. The device of clause 24, wherein the graphical representation of the information comprises a physiological waveform generated based on the received information.

Clause 26. The device of clause 24 or clause 25, wherein the graphical representation comprises an indication of one or more of patient physiological status for the time or range of times defined by the slider, an indication of patient activity for the time or range of times defined by the slider, and/or an indication of device status for the time or range of times defined by the slider.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION

As used herein, the singular form of "a", "an", and "the" include plural referents unless the context clearly dictates otherwise. It is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to devices and methods for receiving, processing, and displaying information from a medical device, such as a wearable therapeutic device or a patient monitoring device. Physiological information can be received from a medical device and displayed to a remote technician or reviewer (e.g., a trained analyst at a central location) in the form of a list of available data recordings for short time periods within a total monitoring time interval. For example, the reviewer analyzing cardiac data may see a list of available ECG recordings or heart sounds recordings for short periods of time (e.g., about 30 to 60 seconds or longer per recording) within the total time interval. However, patient information for "gaps" between the recordings is generally not readily available for viewing by the reviewer. The present disclosure relates to devices and processes for providing visual representations for the "gaps" between available recordings based on information collected by the medical device to assist the reviewer in appreciating patient condition and device status during the gaps and, in particular, for periods of time just prior to or following time periods covered by available recordings.

Figure 1:
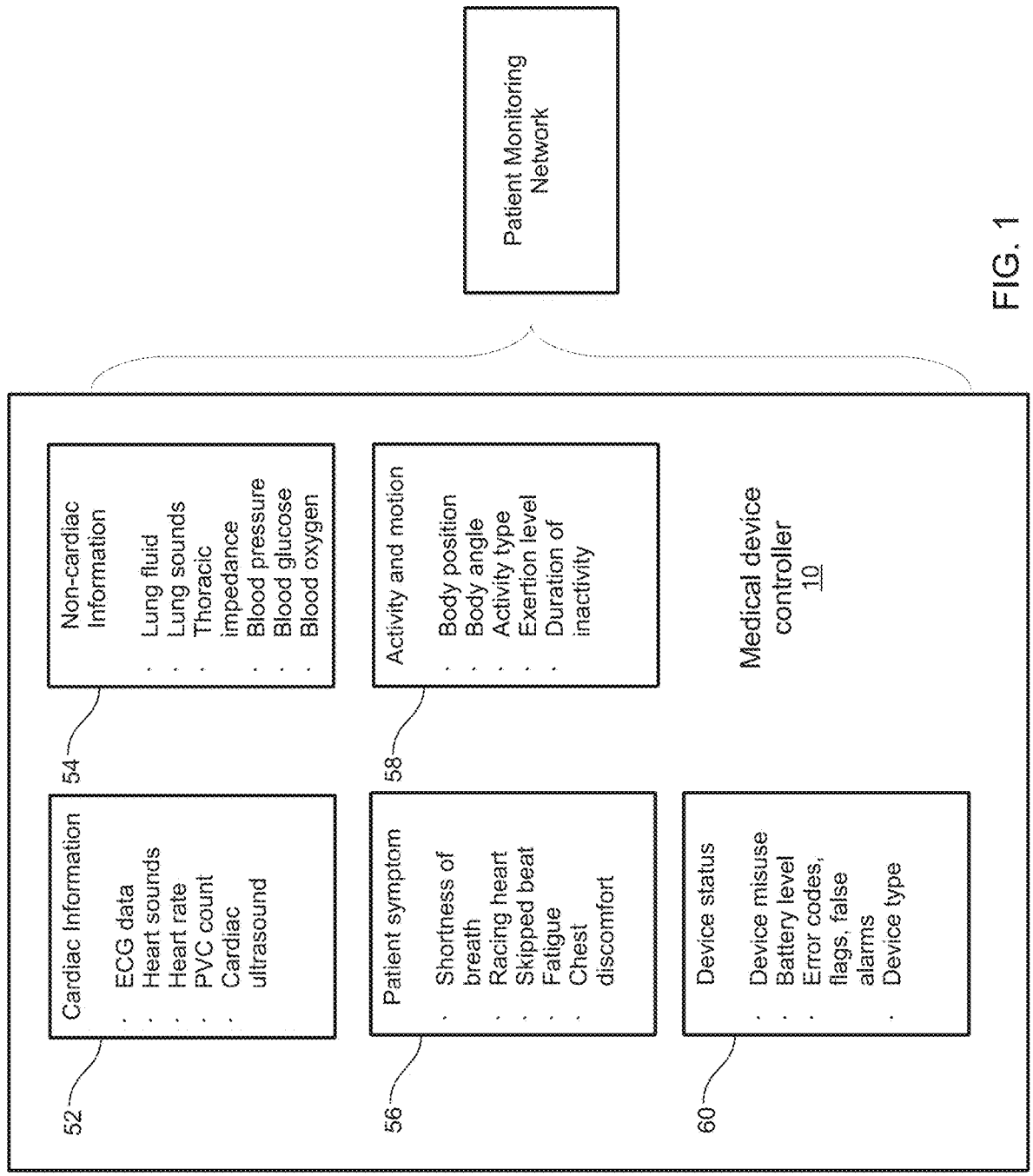
FIG. 1 is a flow chart depicting categories of information collected by a wearable medical device.

With reference to FIG. 1, information received by a patient monitoring network from a medical device controller 10 that can be used for generating visual representations can include monitored cardiac information 52, monitored physiological (non-cardiac) information 54, patient reported symptom information 56, patient activity and motion information 58, and device status information 60. Examples of types of information within each category are shown, for example, in FIG. 1. Cardiac information 52 received from the medical device can include, without limitation, ECG data (e.g., long-duration or short-duration ECG recordings, along with associated annotations and/or fiducial data of interest), premature ventricular contraction (PVC) count, heart rate information, heart sounds information (e.g., data received from Audiocor® sensors manufactured by Inovise Medical, Inc. of Beaverton, Oreg.), and cardiac ultrasound data. The received physiological information can cover a plurality of time segments within a predetermined time interval. For example, individual time segments may comprise cardiac data, such as ECG recordings, for 30 seconds, 45 seconds, 60 seconds (1 minute), 2-3 minutes, or longer, taken over, for example, a 24-hour time interval. Certain cardiac data, such as heart rate data, does not need to be collected at a high sampling rate. Instead, such data can be measured periodically (e.g., every 5 minutes, 10 minutes, or 15 minutes) to provide an indication of general changes in heart rate over time. Accordingly, heart rate information can be provided for the entire time interval rather than for short duration segments.

Patient symptom and response information 56 can include patient survey results (e.g., patient answers to questions about symptoms). For example, patients can report shortness of breath, heart racing, feeling a skipped beat, fatigue, fainting, or chest discomfort. Patients can report symptom information using one or more input components (e.g., buttons, trackpads, touch screen displays) associated with the medical device. Patient response information comprises results from tests or tasks performed by the patient (e.g., 6-minute walk test or other physical activity test results). Patient symptoms and results can be provided either at predetermined intervals (e.g., the device is configured to ask a series of questions to the patient at a predetermined time) or as controlled by the patient. For example, the patient may enter symptom information when he or she experiences symptoms and may choose to perform various tasks or tests at convenient times. In some examples, the medical device or medical device controller 10 can obtain a recording of cardiac information 52 (e.g., a short duration ECG recording) when the patient identifies symptoms with the device controller 10 (e.g., in response to survey questions). In other examples, the device controller 10 may provide survey questions to be answered by the patient when a cardiac event is identified based on analysis of sensed cardiac information. In either case, patient symptom information 56 is recorded along with, and often in response to, recording of cardiac data by the medical device. As such, patient symptom information 56 can be considered to be information related to patient cardiac function and, according, can be displayed along with the recorded cardiac data.

Cardiac information may also include information related to frequency or susceptibility to false alarms issued by the device or device controller 10. As described herein, false alarms can be generated in response to issues of signal quality for sensed physiological signals. For example, a false alarm can be generated as a result of a noisy ECG signal.

In some examples, non-cardiac information can include, for example and without limitation, non-cardiac physiological information 54, activity and motion information 58, and device status information 60. Monitored non-cardiac physiological information 54 can include lung fluid measurements/data (e.g., based on radio-frequency sensors), lungs sounds data (e.g., based on audio sensors), patient thoracic impedance measurements/data, pectoral impedance measurements/data, blood pressure, temperature, blood glucose levels, and blood oxygen levels. Many of these data measurements can also be obtained periodically throughout the entire time interval, which can be a number of hours or days.

Patient movement and activity information 58 can include patient body position (e.g., movement, upright, reclined, lying), body angle while reclined or lying, body position while reclined or lying (e.g., movement, left, prone, supine, right), a type of activity being performed by the patient, the patient's level of physical exertion, or an amount of time of relative inactivity. Device operating status 60 information can include information about how the patient is using the device (e.g., device use or misuse information), as well as battery level information and information about numbers of error codes, flags, and other events issued by the device. Patient symptom information 56, activity information 58, and device status information 60 can be collected periodically or in response to an action by the user or device.

Information received from the medical device can include data sampled at high resolution for short periods of time for cardiac physiological parameters, such as patient ECG. For example, the medical device may record and transmit ECG recordings for time periods including identified cardiac events. The medical device may transmit information about patient and device status obtained from other sources along with the ECG recordings. In some implementations, the data may be time-stamped and source-authenticated to indicate an origin of the information. In some implementations, such information can include ECG data in combination with tissue fluid data, patient position and/or motion information, and/or device parameters (e.g., device parameter values, threshold levels, battery information, etc.).

The medical device controller 10 can also be configured to record and periodically transmit lower resolution data for physiological parameters, such as non-cardiac physiological information 54, having a lower degree of variability. Heart rate information can also be collected and transmitted in this manner. Often such data transmissions include data from a single source without corresponding data from other sources. Such low resolution data can be used for filling in "gaps" between short duration high resolution data segments (e.g., ECG recordings).

The devices disclosed herein are configured to receive information from the medical device or medical device controller 10. The received information covers a predetermined time interval and includes information related to occurrences of cardiac events and/or non-cardiac events. For example, the information received from the medical device can include one or more ECG recordings and/or one or more recordings sensed by heart sound sensors. The recordings can be processed or analyzed to identify the cardiac events. The devices disclosed herein may also receive data related to non-cardiac events, and may correlate a time of occurrence or time period of the cardiac events and the non-cardiac events. Processing information received from the medical device can also include identifying gaps in the ECG recordings during the predetermined time interval and reconstructing ECG recordings during the gaps based on the received non-cardiac data. The processed information can be used to generate one or more graphical representations for the time interval based on the cardiac event and the non-cardiac events.

In some implementations, such reconstructions can be based on causing various cardiac and non-cardiac events to be graphically represented in a coordinated manner (e.g., on a same timeline). Accordingly, in some implementations, a reviewer is presented with a comprehensive overview of patient and device status for the predetermined time interval. In some examples, the generated graphical representation can include sections based on cardiac information (e.g., sections based on recorded ECG signals) in combination with sections generated based on information about non-cardiac events.

In some applications, the generated graphical representations can be provided to service technicians to assist the technicians in troubleshooting certain problems with medical devices being worn by patients. The generated representations can also be used by reviewers tasked with confirming or verifying various alerts and events output or identified by the medical device and, in some cases, to assist reviewers in preparing patient reports including annotated or selected data for the patient over the time interval. The generated patient reports can be provided to physicians or other caregivers so they may make determinations about the patient's condition and assess options for continued treatment.

Figure 2:
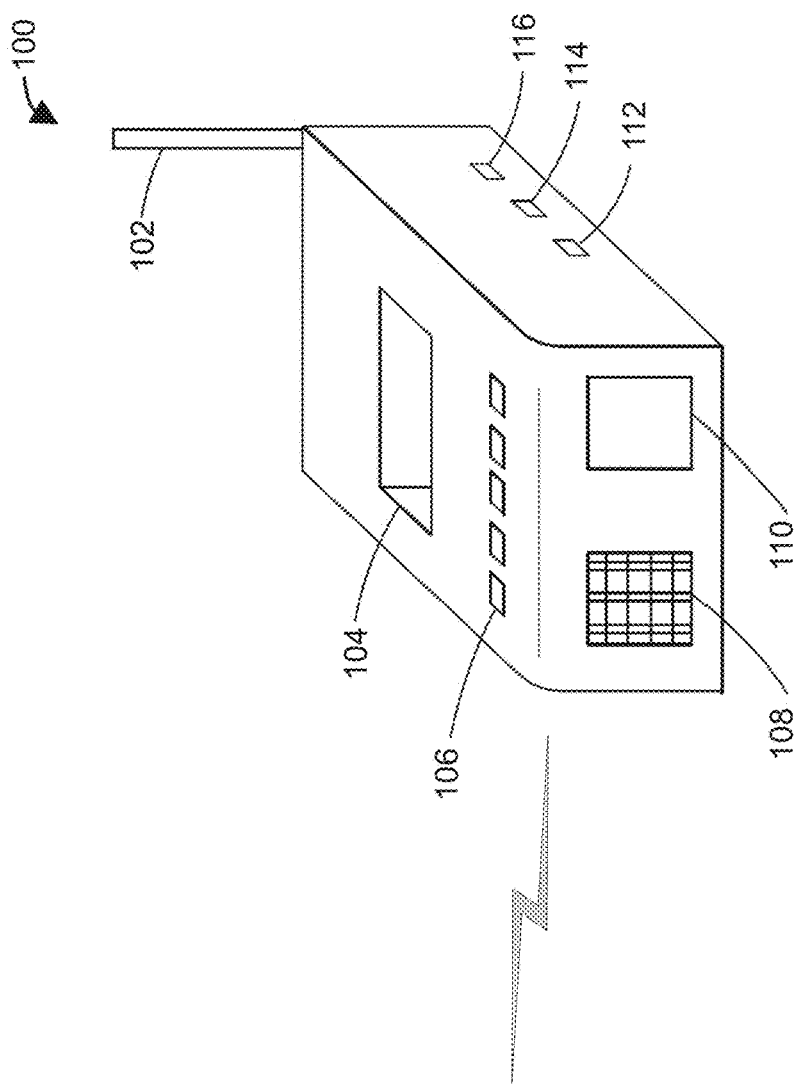
FIG. 2 is a schematic drawing of a medical device controller and base station according to an aspect of the disclosure.
Figure 2:
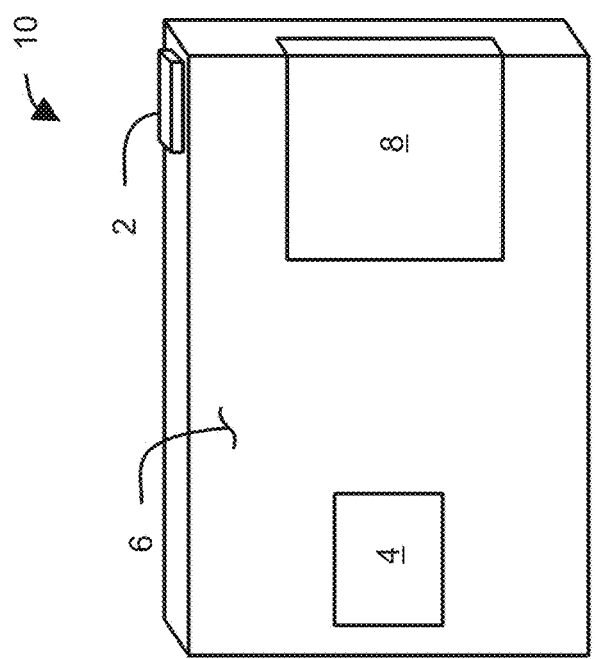
Figure 3:
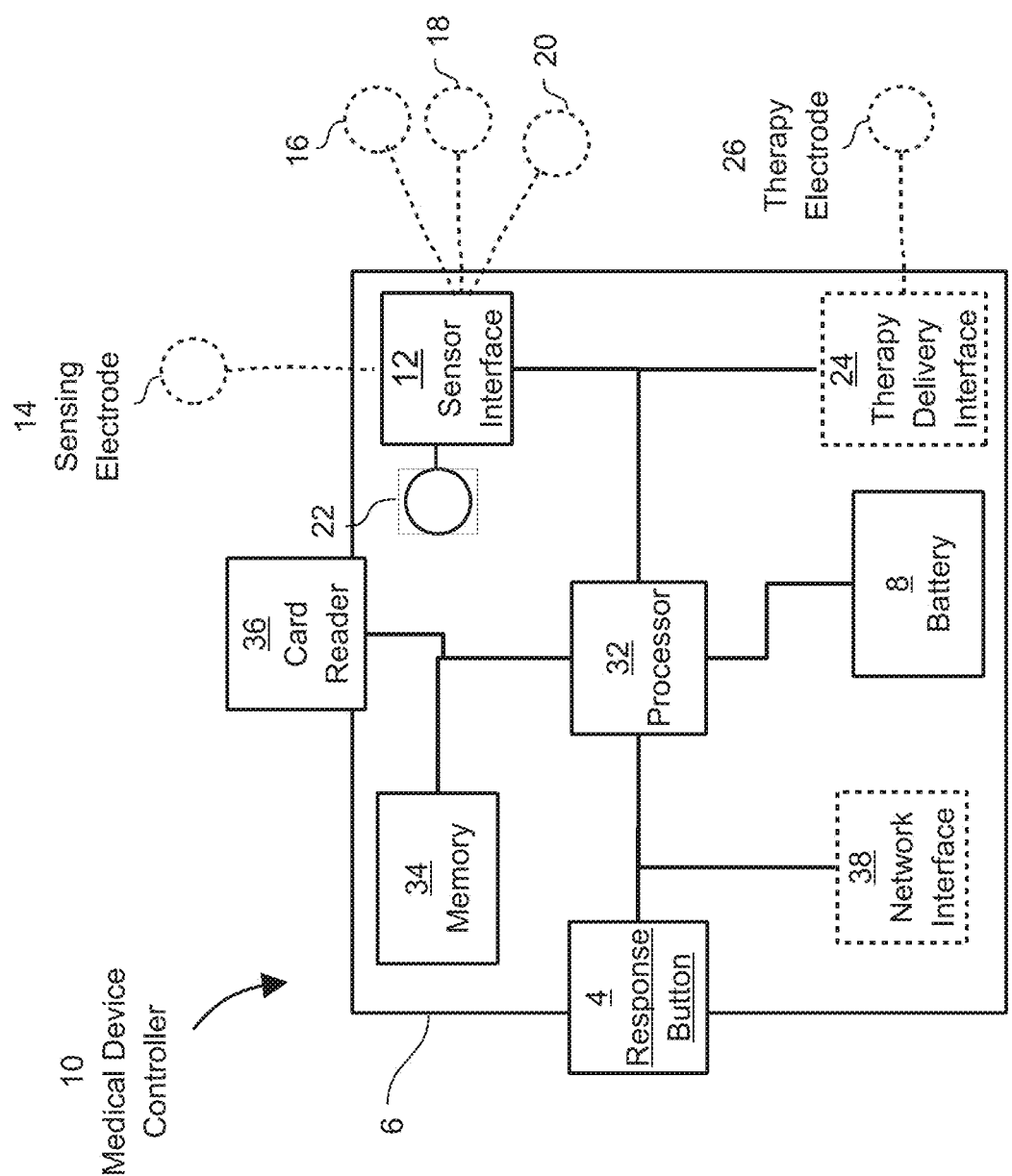
FIG. 3 is a schematic drawing of the medical device controller of FIG. 2.
Figure 4:
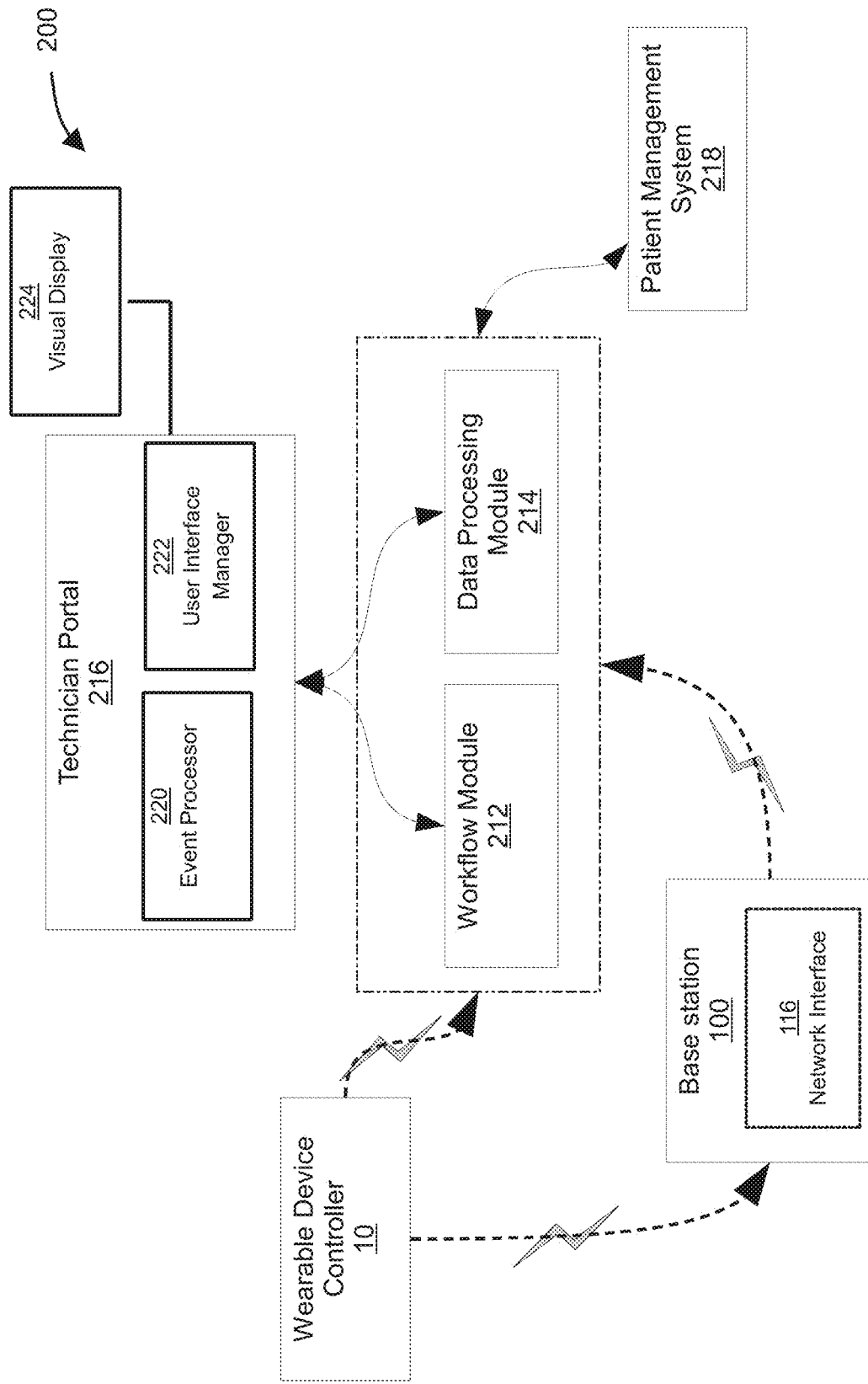
FIG. 4 is a schematic drawing of a medical information network including the medical device controller of FIG. 2.

Example Therapeutic Medical Device:

With reference to FIGS. 2, 3, and 4, an external medical device can include a controller 10 as illustrated. For example, the external medical device can be a non-invasive medical device configured to be located substantially external to the patient. Such a device may be, for example, an ambulatory device that is capable of and designed for moving with the patient as the patient goes about his or her daily routine. For example, the medical device as disclosed herein can be bodily-attached to the patient such as the LifeVest® wearable cardioverter defibrillator available from ZOLL® Medical Corporation. Such wearable defibrillators typically are worn nearly continuously or substantially continuously for an extended period of time (e.g., a period of time extending to a few or several hours, days, weeks, months, or more). That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). During the period of time in which they are worn by the patient, the wearable defibrillator is configured to continuously or substantially continuously monitor the vital signs of the patient and, upon determination that treatment is indicated, is capable of delivering one or more therapeutic electrical pulses to the patient. For example, such therapeutic shocks can be pacing, defibrillation, or transcutaneous electrical nerve stimulation (TENS) pulses. Non-limiting examples of suitable wearable defibrillators are disclosed in U.S. Pat. Nos. 5,078,134; 6,681,003; and 8,271,082, each of which is assigned to the assignee of the present application and is incorporated by reference in its entirety.

The controller 10 comprises a housing 6 with openings for accessing one or more ports 2 (shown in FIG. 2). Sensors, sensing electrodes, and/or therapeutic electrodes for obtaining data from and providing treatment to the patient can be removeably connected to the controller 10 through the one or more ports 2. The controller 10 further comprises response button(s) 4 that receive patient responses to alarms or alerts provide by the controller 10. Specifically, the patient can press the response button(s) 4 to suspend or withhold treatment if he or she is conscious and no treatment is indicated. In some examples, the controller 10 is powered by a rechargeable battery 8.

With specific reference to FIG. 2, the medical device controller 10 can be in communication via a wired or wireless communication link with a base station 100 capable of performing a number of different functions. In one example, the base station 100 acts as a communications link (e.g., a WiFi hotspot or Bluetooth link) for the controller 10.

Specifically, the base station 100 can be configured to wirelessly receive data from the controller 10 via a wireless data transmission via WiFi or Bluetooth technology. The base station 100 can be configured to wirelessly transmit the received information to a remote source, such as a remote computer server, e.g., via a wireless cellular network.

As illustrated, the base station 100 comprises an antenna 102, a battery charging bay 104 capable of charging the rechargeable battery 8, and one or more communication interfaces 112, 114, and 116 to receive information from the controller 10 and to communicate the received information to the remote computer network or server. For example, the medical device controller 10 can provide information about the patient's medical condition and/or about the status of the medical device to the base station 100. The base station 100 can store and, at an appropriate time, communicate the information via communication interfaces 112, 114, 116 to the remote network. In some examples, data transmission can be actuated manually by, for example, pressing one of the buttons 106.

Having described the external features of the controller 10 and base station 100, internal circuitry of the controller 10 will now be discussed in greater detail with particular reference to FIG. 3. As shown in FIG. 3, the controller 10 comprises a plurality of sensors for monitoring the condition of the patient, medical device, and controller 10. The sensors are in electronic communication with a sensor interface 12, which is configured to receive and process signals therefrom. Exemplary sensors can include sensing electrodes 14 (e.g., ECG electrodes), contact sensors 16, pressure sensors 18, accelerometers or motion sensors 20 (e.g., a single axis accelerometer, a multi-axis accelerometer, or a gyroscope), and location sensing circuitry 22 (e.g., GPS circuitry). Other sensors, such as tissue fluid monitoring sensors, humidity sensors, moisture sensors, temperature sensors, pulse oximetry sensors, blood pressure sensors, and cardiac audio sensors (e.g., heart sounds sensors) can also be connected to or associated with the medical device controller 10. Additionally, the controller 10 can include a therapy delivery interface 24, which is coupled to one or more therapy electrode(s) 26.

The controller 10 further comprises a processor 32 electronically coupled to the sensor interface 12 and the therapy delivery interface 24. The processor 32 is also in electronic communication with transitory or non-transitory computer readable memory 34 for storing information received from the sensors. The computer readable memory 34 can also comprise instructions for the processor 32 that, when executed, cause the processor 18 to perform the following functions. For example, the processor 32 can be configured to identify or determine events or flags related to patient condition or device operation based on analysis of data and information received from the sensor interface 12.

Examples of events, alarms, alerts, or flags that can be identified by the processor 32 include cardiac physiological events (e.g., identification of bradycardia, ventricular tachycardia, ventricular fibrillation, or premature ventricular contractions (PVCs) based on analysis of obtained ECG recordings). The processor 32 can also identify non-cardiac physiological events based on information collected from other types of sensors (e.g., alerts based on lung fluid measurements, patient thoracic impedance measurements, pectoral impedance measurements, blood pressure, temperature, blood glucose levels, and blood oxygen levels.).

The processor 32 can also be configured to identify non-cardiac events related to patient motion and physical activity based on information received from motion sensors and/or accelerometers. For example, the processor 32 can be configured to identify one or more of patient body position, body angle while reclined or lying, body position while reclined or lying, a type of activity being performed by the patient, the patient's level of physical exertion, or an amount of time of relative inactivity. The processor 32 can be configured to issue an alert or identify an event if an unexpected or undesirable result related to body position or patient movement is identified.

In other examples, the processor 32 can be configured to identify device-initiated events, such as when a defibrillator shock (e.g., a treatment event) is provided to the patient or abnormal diagnostic test results for the medical device and/or controller 10. In other examples, the processor 32 can be configured to identify non-cardiac events including device malfunctions, such as a lost electrode signal event (e.g., electrode falloff), electrode noise event(s) (e.g., noisy ECG signal received from one or more electrodes), and/or abnormal device shutoff events.

For example, the processor 32 may identify electrode falloff according to the following process. The processor 32 may cause therapeutic electrodes 26 to provide an electromagnetic signal (e.g., in the form of an 800 Hz square wave) onto the patient. The ECG electrodes 14 can detect the signal as it passes through the patient's body. The processor 32 can read the detected signal. In certain implementations, the sensed signal is present only when the ECG electrodes 14 have good contact to the patient. If the ECG electrode(s) 14 is off of the patient the value detected by the ECG electrodes 14 and read by the processor 32 will be approximately 0V. In a similar manner, the processor 32 can identify falloff of the therapeutic electrodes 26 based on sensed patient impedance. If a voltage outside of normal patient impedance is sensed, the processor 32 may determine that therapeutic electrodes are off and are not in good contact to the patient.

In other examples, the processor 32 can be configured to identify non-cardiac events caused by instances of device misuse. For example, signals from the accelerometers or motion sensors 20 can be monitored to determine if the patient has dropped or mishandled the medical device and/or controller 10.

In other examples, rather than recording information in response to identification of certain events, the processor 32 can be configured to record device and physiological information periodically according to a predetermined schedule (e.g., once every 15 minutes, once every hour, or once every 24 hours). In other examples, events can be manually or remotely triggered. For example, the patient can initiate obtaining a recording (e.g., a patient initiated event) by selecting an appropriate option on a touch screen display of the controller 10 or by pressing the response button(s) 4. In other examples, an event can be triggered remotely (e.g., server triggered recording) by a signal received by the network transmission component and/or from the base station 100 (shown in FIG. 2).

Following detection of the event, the processor 32 is configured to record and/or preserve sensor data and other information for periods of time immediately preceding and/or following the identified event. For an identified cardiac event, the sensor data can comprise an ECG recording of a predetermined limited duration (e.g., about 45 seconds or one minute following the event). The recorded data segment can also include information from the other sensors associated with the controller 10 and/or patient, as well as manually entered information, such as patient symptom information. This data can be stored in the computer readable memory 34 associated with the processor 32 for transmission to the remote server at a later time (e.g., as part of a batch download including multiple data segments) or can be transmitted to the remote server immediately. The controller 10 can also continuously store information for an entire time interval that the wearable medical device is in use. In an implementation, such data may be continuous ECG data without corresponding data from other sources. For example, an ECG signal can be continuously recorded and stored on a removable media card, e.g., a secure digital (SD) card, inserted in a card reader 36 associated with the controller 10. In some examples, the SD card can be configured to store ECG data for 30 days or longer.

With continued reference to FIG. 3, the controller 10 further comprises a network interface 38 for transmitting information between the controller 10 and one or more other devices or entities as described above. For example, the network interface 38 can be used to transmit stored data to the remote server or device for further analysis or review. For example, the controller 10 may be configured to transmit the data directly to a server (e.g., a remote server) where a service representative, technician, reviewer, physician, or caregiver can access the transmitted information. In other examples, the network interface 38 can be configured for short-range data transmission over a data transmission protocol, such as Bluetooth® or Zigbee. For example, the network interface 20 can transmit data to the base station 100 when the controller 10 is in close proximity thereto.

By way of example, a process followed by the controller 10 for identifying a cardiac event, providing treatment to the patient (e.g., a treatment event), and storing data related to the identified event, will now be described. In some instances, the processor 32 is configured to determine that the patient is experiencing a cardiac arrhythmia and that a shockable rhythm is present. Upon determination that a shockable rhythm is present (e.g., ventricular tachycardia, ventricular fibrillation, among others), the processor 32 is configured to begin preparing the medical device to provide treatment. The controller 10 can instruct the patient to press and hold one or both of the response buttons 4 to indicate that he or she is conscious, thereby instructing the medical device controller 10 to withhold the delivery of therapeutic defibrillating shocks (e.g., a false alarm). If the patient does not respond to an instruction from the controller 10, the controller 10 can determine that the patient is unconscious and proceed with the treatment sequence, culminating in the delivery of one or more defibrillating shocks to the body of the patient. Following the treatment sequence, the processor 32 is configured to obtain and store information from sensors related to the identification of the arrhythmia and treatment. The information can include, for example, the ECG trace of the time period, as well as other physiological measurements for the time period. The information can also include an indication of the type of event, outcome, and associated details. For instance, the information stored may indicate whether the event was resolved without treatment being provided (e.g., in the case of a false alarm), whether the event was due to a device malfunction, or, whether the event resulted in treatment being provided. If treatment was provided, the information may include details regarding the nature of the treatment, including number of pulses and energy level of each pulse, and an indication of whether sinus rhythm had returned. The information is saved to the memory 34 and transmitted to an appropriate server or device by the network interface 38 at an appropriate time. It is noted that the processor 32 can also be configured to create a record of sensor information if the patient presses the response button(s) 4 without being prompted by the controller 10. Such an unprompted button press may indicate that the patient is unfamiliar with how to operate the controller 10 and/or is confused about the purpose of the response button(s) 4. Recorded information about patient and device status can be reviewed to assess reasons for the unprompted button press.

Exemplary Patient Monitoring Device

In some examples, the medical device can be a non-therapeutic patient monitoring device for an ambulatory patient, such as cardiac event monitoring (CEM) device or mobile cardiac telemetry (MCT) device. CEM devices collect cardiac information, such as a patient electrocardiogram (ECG) data, and provide the information to an external network or remote server on a periodic basis. Mobile cardiac telemetry (MCT) devices monitor patient physiological information, such as ECG, and send data aperiodically, such as when a particular triggering event is identified. MCT devices can further comprise additional sensors for measuring non-ECG physiological parameters. Data from non-ECG sensors can be provided along with ECG recordings for identified events.

CEM and MCT devices are used for monitoring patient cardiac function for a predetermined interval (e.g., a number of days or weeks) to provide information about frequency and duration of cardiac events experienced by a patient. Cardiac events that can be identified by patient monitors can include, without limitation, one or more of atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. The collected information about identified cardiac events can be used, for example, to produce patient reports for time periods of interest. The devices and methods for visualizing information received from medical devices described herein can be used to assist a reviewer in preparing patient reports. In some implementations, the patient can interact with a user interface of the patient monitor to identify one or more patient symptoms. The user interface may include a touchscreen that provides a drop down menu or check list which, in turn, allows the patient to select a particular symptom from a list of alternatives. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the patient monitor can cause a portion of patient physiological information (e.g., in the form of a cardiac signal) to be captured for a length of time that is based on when the symptom was experienced. For example, the patient monitor can cause a portion of an ECG signal of the patient to be captured. The portion of the ECG signal that is captured can be associated with the reported symptom and patient information.

Patient reports prepared by reviewers can include ECG traces for identified events. Patient reports can also include certain cardiac overview information (e.g., a percentage of time that a patient has tachycardia or fibrillation per day). Patient reports can be prepared periodically (e.g., daily or weekly). Patient reports can also be prepared when cardiac events of interest are identified by the monitoring device. Reports can also be prepared at the end of a monitoring interval and include information about all events identified over the monitoring period. The prepared patient reports are provided to a prescribing physician for use in determining appropriate patient treatments.

A patient monitor (e.g., an MCT device) can include a controller, similar to the controller 10 shown in FIGS. 3 and 4, though without the therapeutic components of the controller 10. The patient monitor controller can be communicatively coupled (e.g., wired or wirelessly coupled) to sensors and/or electrodes appropriately positioned on patient to obtain signals (e.g., ECG data and/or heart sounds data from an acoustic sensor) indicative of cardiac activity. In some examples, the patient monitor controller can, in addition to cardiac monitoring, perform monitoring of other relevant patient parameters, e.g., weight, glucose levels, blood oxygen levels, and blood pressure. The patient monitor controller can also comprise motion sensors to track patient movement. In some examples, the patient monitor can be in the form of an application on a handheld device, such as a smartphone, a personal digital assistant, or a tablet device.

The patient monitor can also include a physiological data processing component for collecting and conditioning the physiological data prior to storing the data locally at computer-readable storage media on the monitor itself and/or transmitting the data to a remote server or device. In some examples, the patient monitor controller further comprises a user interface module that allows the patient to manually enter information about a patient condition, and to initiate sending information to the remote server.

The patient monitor also comprises communication circuitry for communicating with the remote server (e.g., one or more computer systems) over a communications network in the manner described above in connection with the medical device controller 10.

Medical Information Network

With reference to FIG. 4, a network 200 for receiving information and data from the controller 10, patient monitor device, and/or base station 100 is illustrated. The network 200 can include a wired network, a long range wireless network (WiFi), a short-range wireless network (BLUETOOTH®), a cellular network, and/or combinations thereof for transmitting data from the medical device controller 10 and base station 100 to the network 200, between network modules 212, 214, from the modules 212, 214 to a technician portal 216 (or reviewer portal), and, following automated and/or manual review of the information, to a patient management system 218. Information can be sent from medical device controller 10 over the communications network 200 substantially continuously, periodically (e.g., every hour, two others, etc.), aperiodically, upon establishment of pairing with a base station 100, according to a predetermined schedule (e.g., once every 24 hours), or as a result of a request by the patient or from a remote party such as a treating physician. Information can also be transmitted from controller 10 automatically based on data transmission instructions stored on the processor 32 and/or computer readable memory 34 (shown in FIG. 3). Information can be sent from the base station 100 to the network 200 in a similar fashion by communications interface 116.

In some examples, the network 200 comprises a workflow module 212 and a data processing module 214, each of which are configured to receive and process information obtained the medical device controller 10. The workflow module 212 is configured to receive information from controller(s) 10 and to forward the received information to a technician portal 216 for review by a technician or reviewer responsible for a particular patient and/or medical device. For example, the module 212 may be configured to receive information from a plurality of different medical devices and patient monitors, evaluate or associate the received information with a specific patient and medical device or patient monitor, and provide the information to a technician portal 216 for a technician or reviewer responsible for the respective patient and/or medical device. The workflow module 212 may also perform various pre-processing routines to place the received information in a condition that can be reviewed by the technician or reviewer, such as converting the information to a format that is easily manipulated by the technician or reviewer.

The data processing module 214 is configured to automatically analyze the information, such as an ECG signal, using algorithms that provide an indication of patient status and/or cardiac function. For example, a non-limiting list of trends and/or other statistics that can be calculated based on information received from the medical device include: premature ventricular contraction (PVC) count, heart rate information, R-R intervals, heart rate variability, atrial fibrillation (AF) burden, statistics relating to heart sounds data (e.g., chest movement statistics, snoring statistics, and/or lung sounds statistics), lung fluid statistics, patient thoracic impedance measurements/data, pectoral impedance measurements/data, and/or changes in blood pressure, temperature, blood glucose levels, and blood oxygen levels. The calculated trends and/or other statistics can be forwarded to the technician portal 216 or to workflow module 212 to assist the technician or reviewer in analyzing the received information. Alternatively, the trends and/or calculated statistics can be appended or added to any reports or analysis documents prepared by the technician or reviewer and included in a patient or device record stored on or made available through the patient management system 218.

It is noted that the workflow module 212 and data processing module 214 can interface in any manner with the medical device controller 10 and/or base station 100. For example, data from the controller 10 can first be processed by the data processing module (e.g., certain analysis can be carried out on the incoming physiological data prior to providing the information to the technician portal 216) and then passed along to the workflow module 212 for further analysis and interpretation in accordance with the disclosure herein. Conversely, data can be forward to the technician portal 216 with only minimal processing or analysis by the modules 212, 214. After review by the technician or reviewer is complete, the received information can be processed by the modules 212, 214 to provide an additional level of analysis and evaluation.

In an implementation, the following process may be used for uploading data from the medical device controller 10 or base station 100 to the network 200 and/or the patient management system 218. For example, the medical device controller 10 or base station 100 can perform an HTTP POST to upload the data, e.g., in the form of one or more electronic files. The files can be uploaded into event directories on the server, e.g., categorized by a type of file. For example, files can be categorized by an event type which caused the information to be recorded, such as "Afib," "Vfib," "devicefault," "treatment," "manualreport," or "dailyreport". One or more file parsing functions can be called to parse the files for extracting and storing the data in one or more tables in a database on the server. For example, events data can be stored in an events table within a database located on the server. In a similar manner, ECG data can be stored within an ECG table, data collected from other types of sensors, detector, or monitors, can be stored in other appropriate tables, and reported, analyzed, or processed data, that includes events identified by processing algorithms, can be stored in respective reports tables.

With continued reference to FIG. 4, the technician portal 216 allows the technician or reviewer to view the received information for the purpose of identifying and/or confirming any of a number of patient conditions and/or events. For example, the technician or reviewer can review the received information to evaluate performance of the medical device and patient status during the time interval. Based on the evaluation, the technician or reviewer can draw conclusions about why a particular event was identified by the medical device controller 10, causation information about the identified event, medical precursors for the identified event, and whether the medical device is operating in a substantially correct or expected manner. The technician portal 216 can be a computer workstation, desktop computer, tablet, smartphone, and/or personal digital assistant. The technician portal 216 comprises an event processor 220 and a user interface manager 222, associated with a visual display 224. The event processor 220 is configured to analyze the received information to identify events in the received information and to generate a graphical representation of the events to facilitate review of the information by the technician or reviewer. The generated graphical representation of the received information is displayed to the technician or reviewer by the user interface manager 222. For example, the user interface manager 222 can be configured to cause the visual display 224 to display the graphical representation. The user interface manager 222 can also be configured to display information for discrete times or ranges of times in association with the graphical representation determined by the event processor 220. The user interface manager 222 can also be configured to receive inputs from the technician or reviewer and to modify the displayed information based on the received inputs.

Exemplary Processing Routines for Event Processor and User Interface Manager

Figure 5:
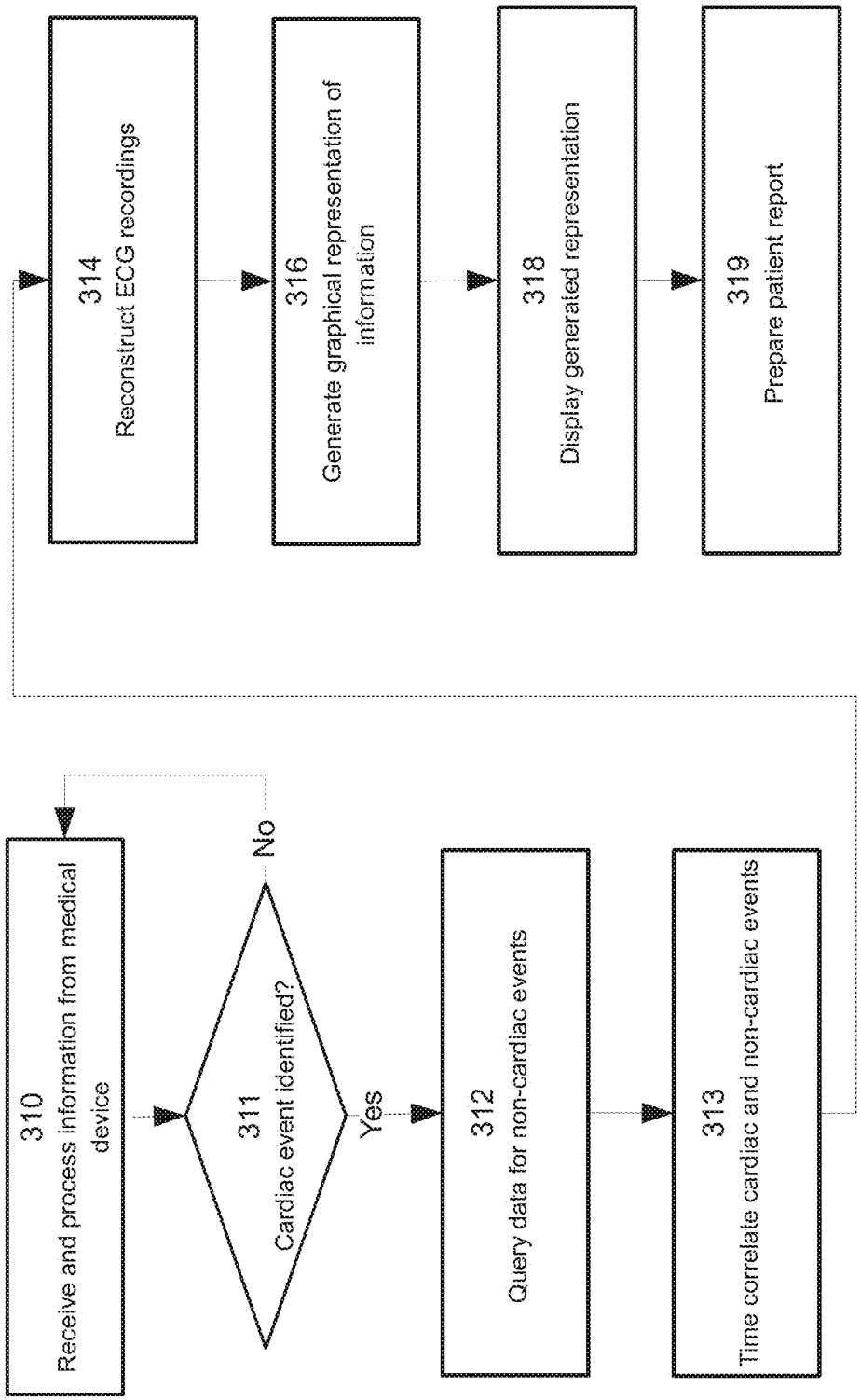
FIG. 5 is a flow chart illustrating a method for generating and displaying a graphical representation of information received from a medical device controller, according to an aspect of the disclosure.

With reference to FIG. 5, processes performed by the event processor will now be described in detail. As shown in box 310, the event processor is configured to receive and process information from the medical device controller over a time interval. As described herein, the received information can include cardiac data, which may include high resolution data, such as ECG recordings or heart sounds data, for certain period of time preceding or following an identified event. Each recording can be about 30 seconds to 2 minutes in length. The recordings can be received from the medical device individually and processed by the event processor sequentially in the order received. In other examples, recordings can be stored on the medical device or medical device controller and sent as a batch download according to a predetermined schedule or, for example, at a convenient time when the device is within range of its base station or a WiFi hotspot. The transmitted recordings can also include information from other sensors and/or manually entered information for the time interval. For example, such information may include non-cardiac physiological information, such as tissue fluid information, as well as patient position and/or patient motion information. The received information may also include device information, such as device flags, device status information, log details, configuration parameter values, monitoring and/or treatment parameter values, battery life information, and capacitor health data. Information received from the medical device can also include low resolution data for time periods between identified events. As described herein, low resolution data includes physiological information that can be sampled at low resolution, as well as patient movement information, manually entered information, and device status information that can be sampled or recorded periodically and relatively infrequently.

As shown at box 311, the event processor is configured to process the received cardiac recordings and other high resolution data to determine and/or identify one or more cardiac events, such as atrial fibrillation onset, atrial fibrillation offset, tachycardia onset, tachycardia offset, bradycardia onset, bradycardia offset. In one example, identification of the event can comprise parsing the received information to identify file structures, file names, or metadata in the received information indicating the type of cardiac event identified by the medical device. In other examples, the event processor can independently analyze cardiac data, such as the ECG recordings, to identify or verify cardiac events in the received ECG data. Other types of information that can be processed for identifying cardiac events can include, without limitation, patient heart rate information, information from an audio sensor positioned adjacent to the patient's heart (e.g., a heart sounds sensor), or other sensor for measuring cardiac function and output. If no cardiac events are identified in the received information, the event processor can continue to monitor received information either continually or on a periodic basis until a cardiac event is identified.

In some implementations, the cardiac events can include manually identified or triggered events, which cause the medical device to obtain a cardiac recording. For example, cardiac events identifiable in received cardiac recordings can include patient-initiated events (e.g., patient initiated recording) and remotely triggered events (e.g., recording triggered automatically by the server and/or manually by a service technician). For patient triggered events, patient symptom information manually entered by the patient may be provided to the event processor in connection with the cardiac data, such as the ECG recordings.

As shown at box 312, the event processor can be configured to process the information received from the medical device controller, including both high resolution data and low resolution data, to identify one or more non-cardiac events represented in the received information. In some implementations, the event processor can be configured to process such events substantially at the same time as the event processor processes cardiac events. Non-cardiac events can include, without limitation, device-initiated events (e.g., treatment performed, ECG electrode falloff, electrode noise events, device self-test results, device battery capacity), and non-cardiac physiological events (e.g., tissue fluid events, blood pressure measurements, pulse oximetry sensor measurements). For example, as discussed herein, electrode falloff can be identified by delivering a voltage waveform to the patient and determining which ECG electrodes correctly sense the delivered signal. The non-cardiac events can occur simultaneously with the identified cardiac events or can occur at a different time.

In some instances, the technician or reviewer can review, verify, and/or confirm event designations determined by the event processor. For example, physiological data related to an event along with the designation for a detected event determined by the event processor can be displayed to the technician or reviewer on the visual display. If the reviewer, after reviewing the event designation and associated physiological data, decides that the automatic designation by the event processor is correct, he or she may confirm the event through the user interface. However, if the technician or reviewer determines that the detected event is designated incorrectly or that no event occurred, the technician or reviewer can manually enter a new designation. For example, he or she can select the correct type of event or can select "No event" from, e.g., a drop-down list.

Once cardiac and non-cardiac events are identified, as shown in box 313, the event processor can be configured to correlate a time of occurrence or time period associated with the cardiac event(s) and times of occurrence or time periods for the non-cardiac event(s). In certain implementations, correlation of cardiac and non-cardiac events can be used for establishing causation or explanation for why certain events occurred. For example, if the cardiac event comprises a false alarm generated as a result of a noisy ECG signal, a reviewer may be directed to consider non-cardiac events correlated in time with the false alarms. For example, such a non-cardiac event may be an electrode fall-off event or an electrode noise event. Such time correlations may be used to assist in identifying non-cardiac events that contribute to the noisy ECG signal. Accordingly, the devices and processes discussed herein can be used to assist a reviewer in determining or understanding causes of the cardiac events, such as the false alarms.

As shown at box 314, the event processor can also be configured to identify the gaps between ECG recordings for the identified time interval and to reconstruct such gaps based on received non-cardiac data. For example, ECG recordings for the gaps can be estimated based on information from other sensors associated with the patient and/or medical device. In one implementation, an estimated or reconstructed ECG recording can be based on patient heart rate. To estimate ECG based on heart rate, positions of R waves for the reconstructed ECG recording can be aligned with the detected heart rate. Further, since no cardiac events were identified by the medical device or medical device controller during the gaps, it may be assumed that the ECG has a substantially normal appearance without arrhythmia during the gaps. In other examples, an ECG recording for the gap can be estimated or adjusted based on patient motion information and/or level of physical exertion. For example, for patients who are exercising and/or moving vigorously, the reconstructed ECG can be adjusted to account for the determined level of exertion.

As shown at box 316, once events are correlated and ECG recordings for gaps are reconstructed, the device can be configured to generate a graphical representation of the processed information based on the cardiac event(s) and non-cardiac event(s). In some examples, the graphical representation can comprise one or more of an event timeline, a histogram, or a three-dimensional chart based on the identified events. In some examples, multiple graphical representations can be generated for the same set of received information. For example, the event processor may generate a timeline based on ECG recordings, a timeline based on patient heart rate, and a histogram based on patient activity (e.g., patient steps) for the received information. In that case, the reviewer or technician may switch between the different graphical representations by, for example, selecting an appropriate button or tab on the user interface display.

In some examples, the graphical representation comprises an event timeline for an entire time interval including portions for which cardiac data (e.g., ECG recordings) is available and portions for which only reconstructed ECG recordings are available. In that case, the timeline includes sections based on recorded ECG signals interspersed between segments generated from reconstructed ECG signals.

In order to differentiate portions of the timeline generated from actual ECG recordings from portions of the timeline using a baseline ECG or an estimated ECG, as noted above, the actual ECG recording portions may have a different appearance (e.g., different color, shade, pattern, or style) compared to the other portions of the timeline. For example, the timeline can further comprise indicia for differentiating sections of the timeline based on ECG recordings and sections of the timeline generated from the reconstructed ECG recordings. In some examples, portions of the timeline based on the ECG recordings can be represented in a first color (e.g., red or black), shade, pattern, or style. Portions of the timeline generated from reconstructed ECG recordings can be visualized with a second color (e.g., yellow or gray), shade, pattern, or style. In some examples, a lighter shade of lines may be used to represent the reconstructed ECG portions, and a darker, bolder shade may be used to represent the sections of the timeline generated from the actual ECG recordings. In some examples, the timeline can be representative of measured physiological signals (e.g., an ECG trace).

In another example, the graphical representation may comprise a histogram. A histogram is a representation of a distribution of occurrences or events over a selected period of time. For example, a histogram could be used to illustrate number of flags, treatment events, false alarms, PVC events, patient steps taken, calories burned, or other features that occur multiple times over the time interval. Other multi-dimensional representations, as are known in the art, for displaying information about the patient and/or device can also be generated by the event processor and displayed by the user interface manager.

As shown at box 318, once the representation is generated, the graphical representation and, in some instances, other information about the time interval is provided to the user interface manager, which is responsible for displaying the received graphical representation and other information to the technician or reviewer. As is discussed hereinafter in connection with FIGS. 7 and 8, the user interface manager can be configured to display the graphical representation of the cardiac and non-cardiac events. The user interface manager can also display visual representations of device or patient status for a specific times or time range within the total time interval. For example, the user interface manager may be configured to display patient physiological values (e.g., heart rate, pulse oximetry level, or blood pressure) for a particular time or time range. The display could also include representations of values for patient movement (e.g., speed, length of time without moving, or body position information) for a selected time or time range. In some examples, as discussed hereinafter, the technician can select or toggle between different times or time ranges and the values displayed on the display can be updated by the user interface manager to correspond to the newly selected time or time range.

As shown at box 319, based on the review of the displayed information, the technician or reviewer can prepare a patient report for the information received from the medical device controller. In preparing the report, the technician or reviewer can, for example, manipulate relevant portions of the physiological information to make relevant portions of physiological information easier for the end user (e.g., a physician, caregiver, or the patient) to identify and review. The technician or reviewer can also edit portions of data, such as segments of an ECG signal, and provide annotations about which portions of the ECG trace show different types of events. The report can also include other patient information, trends, diagnostic information, and/or patient statistics determined from the total time interval and/or total monitoring period (e.g. percentage of time in a particular cardiac condition, total patient wear time, etc.). Other statistics or metrics that can be included in the patient report can include, for example, percentage of time in atrial fibrillation, percentage of time with bradycardia, percentage of time with tachycardia, average heart rate, most common symptom reported by the patient, number of identified events, and a number of treatments by a therapeutic medical device.

Figure 6:
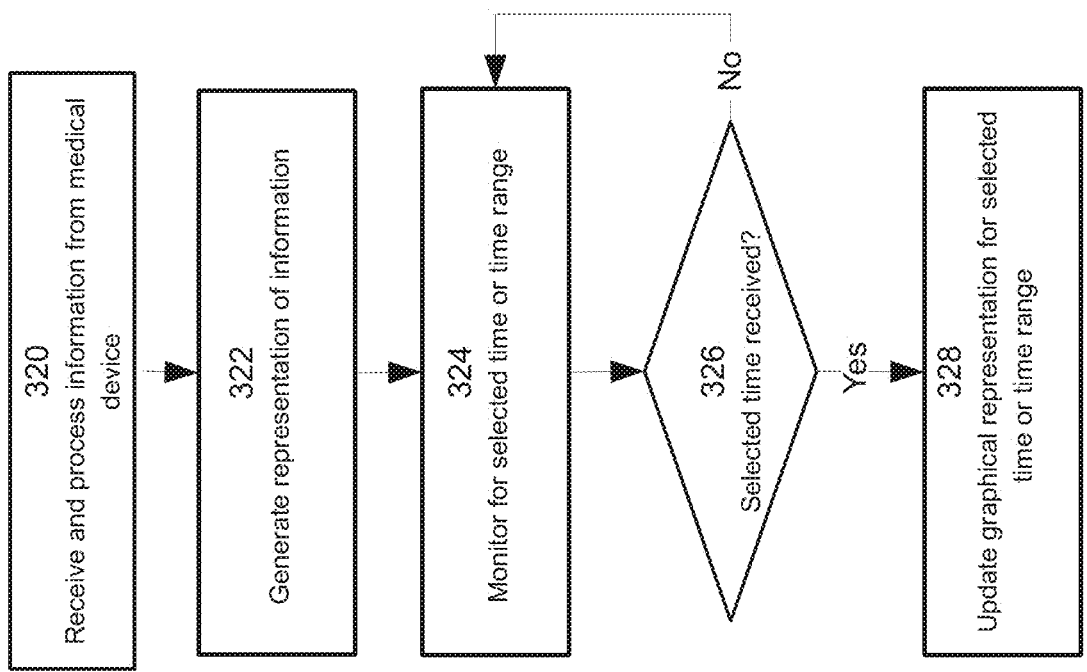
FIG. 6 is a flow chart illustrating a method for displaying a graphical representation of information received from a medical device controller, according to another aspect of the disclosure.

With reference to FIG. 6, steps carried out by the event processor and user interface manager for receiving a selected time or time range and for updating the graphical representation and/or visual display based on the newly selected time or time range are described. As shown at box 320, the event processor is configured to receive and process the information from the medical device and/or medical device controller to identify a plurality of cardiac and non-cardiac events, in the manner discussed above in connection the description of FIG. 5. As shown at box 322, the processed information is used to generate a graphical representation of the received information based on the identified or determined events. The generated graphical representation is displayed to the technician or reviewer by the user interface manager. The user interface manager is also configured to display a selection mechanism on the display screen along with the generated representation to allow the technician to modify or change the information shown on the display. For example, the display screen or user interface can comprise a slider configured to be manipulated by the technician or reviewer. The slider defines at least one time or range of times within the total time interval. Manipulation of the slider (e.g., by changing the position of the slider on the generated representation of the information) selects a new time or time range. As shown at box 324, after the graphical representation is displayed, the user interface manager can be configured to monitor for changes to the selected time or time range, as occurs, for example, when the reviewer or technician changes the position of the slider. For example, the technician or reviewer can use a touch screen display or peripheral computer accessory (e.g., touch pad, keyboard, or mouse) to select a new time or time range. As shown at box 326, the user interface manager is configured to identify and record the selection.

As shown at box 328, once a selection is received, the user interface manager is configured to update the displayed graphical representation and other information to display the newly selected time or time range. For example, the user interface manager may display a different portion of the generated graphical representation. Similarly, the user interface manager may display a different type of graphical representation to show a longer or shorter time period. For example, if a long time range is selected (e.g., a number of hours or days), the user interface may merely display a straight timeline. However, if a shorter time period or a discrete time is selected, the user interface manager may display, for example, an ECG trace or representation of another physiological parameter, such as the patient's heart rate. Further, when a new time or time range is selected, the user interface manager can be configured to update the display to include physiological and/or device status information for the selected time or time range.

Exemplary User Interface

Having described the components of the controller 10, base station 100, and network 200, as well as processing routines for the event processor 220 and user interface manager 222 of the technician portal 216, an exemplary user interface display 400 for reviewing information from the medical device controller will be described in detail. The display 400 can be provided, for example, on the visual display 224 associated with the user interface manager 222 and technician portal 216. In other examples, the exemplary user interface display 400 is provided on a remote device, such as a computer, smartphone, computer tablet, and/or laptop computer wirelessly connected to the user interface manager, so that other individuals, such as caregivers, physicians, or the patient can review the received information and generated graphical representation.

Figure 7:
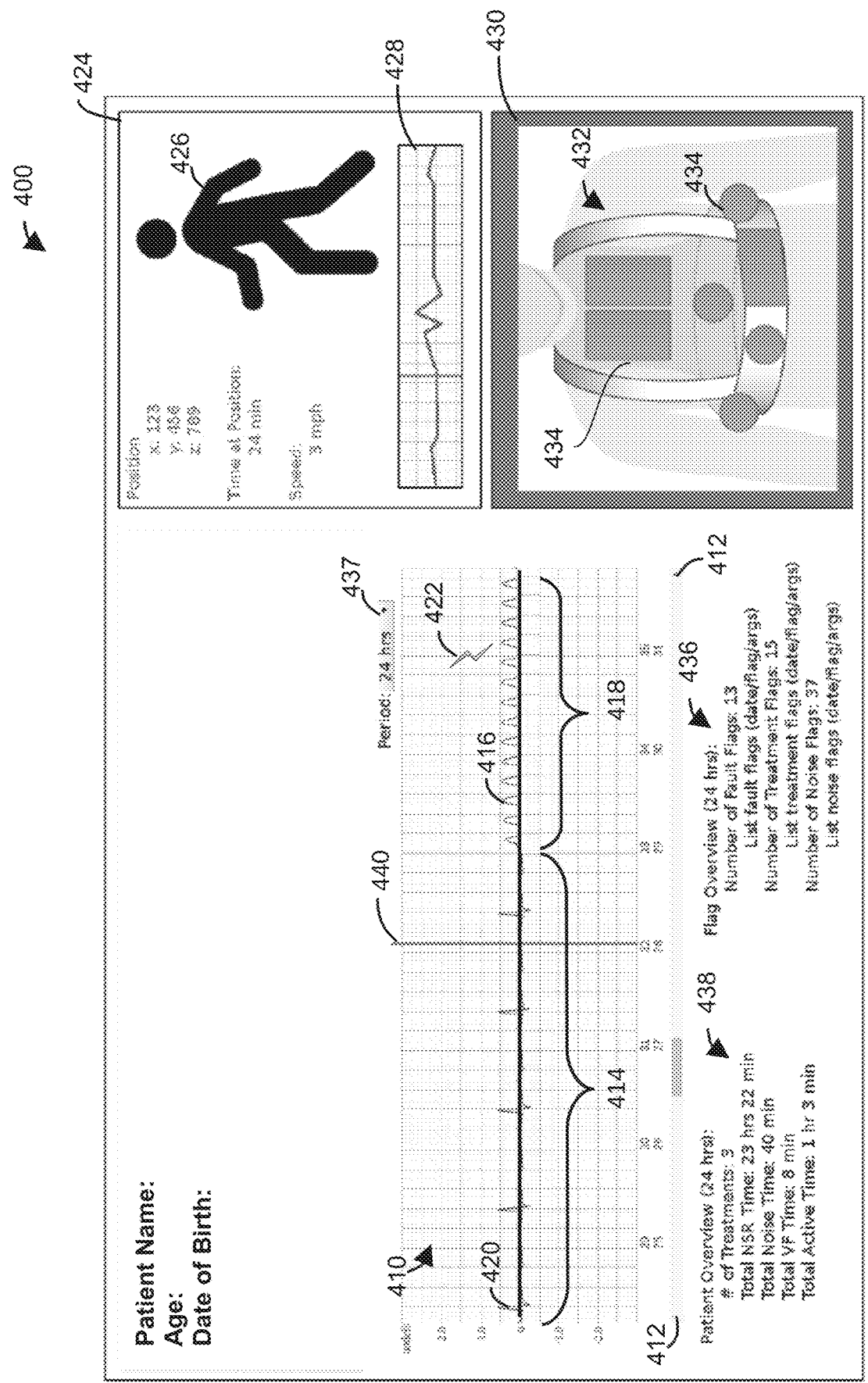
FIG. 7 depicts a user interface display for reviewing information received from a medical device controller, according to an aspect of the disclosure.
Figure 8:
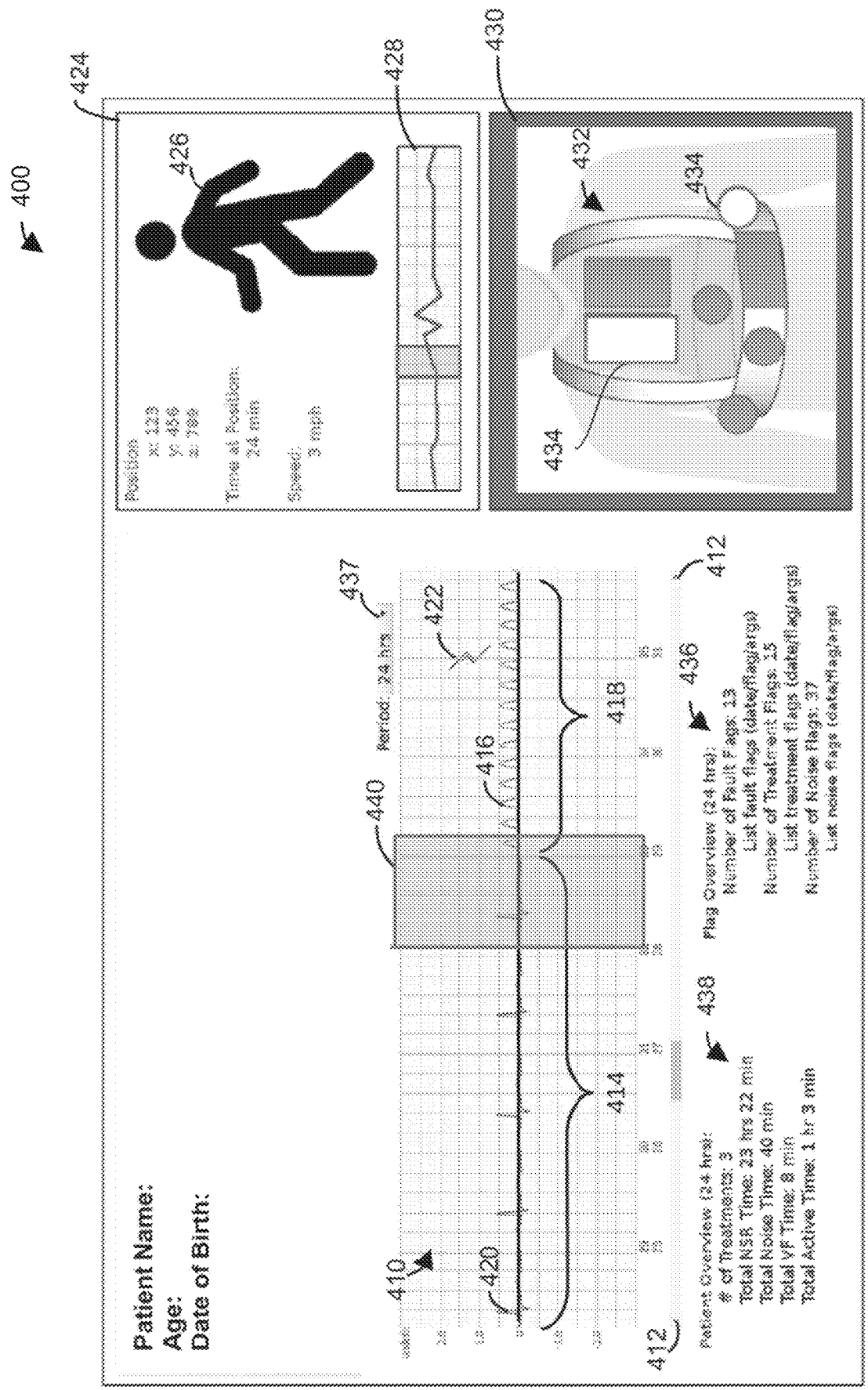
FIG. 8 depicts another view of the user interface display of FIG. 7.

With reference to FIGS. 7 and 8, the user interface display 400 comprises at least one timeline 410 based on ECG recordings and reconstructed ECG recordings for the time interval or for a portion of the time interval included in the information received from the medical device controller 10. For example, the underlying duration represented by timeline 410 can be specified by the reviewer (e.g., using the period selection feature 437 as described below). The reconstructed timeline 410 is an example of a graphical representation based on events identified by the event processor. In some instances, a timeline for the entire time interval can be displayed on the display screen. In other examples, only a small portion of the generated timeline 410 is displayed on the screen at one time. In that case, the technician or reviewer can advance to another portion of the timeline 410 by selecting arrows 412 to move forward or backward along the timeline 410.

In some examples, the timeline 410 comprises a plurality of sections 418 generated based on portions of the received ECG recordings or other cardiac signals, such as heart sounds data. For example, a portion of the timeline 410 based on received ECG recordings may comprise an ECG trace 416 for a period of time covered by the received record. The section 418 may include an ECG representative of an arrhythmia, such as ventricular tachycardia as shown in FIG. 7. The reconstructed timeline 410 may further comprise a plurality of sections 414 for which cardiac information was not received and which are based on reconstructed ECG recordings. These sections 414 can be, for example, periods of time within the time interval covered by the timeline 410 in which no cardiac recordings were received. For example, no notable cardiac events may have occurred at such times/periods, and as such, no cardiac recordings may have been transmitted from the medical device controller to the base station and/or network. In some examples, however, such cardiac information (e.g., ECG traces and other cardiac-related sensor data) for these time periods may be stored locally on the medical device controller and be obtained from the controller at another time, such as when the medical device is returned for servicing or after a course of treatment is completed. In some implementations, such data may also be available to the reviewer or technician on demand (e.g., if the technician or reviewer wishes to see ECG data for a particular period during which no notable cardiac events occurred). As described herein, sections 414 of the timeline, for which no information (e.g., ECG recordings) are available may be represented by one or more of a baseline ECG normal sinus rhythm trace 420 and/or by a placeholder ECG trace (e.g., based on idealized ECG information), an approximation of the patient's ECG trace (e.g., an estimated ECG recording), a composite ECG trace based on the patient's own historical ECG data, a waveform representative of another physiological parameter, or, a generated waveform or graphical pattern that is not intended to convey physiological information. In other examples, portions of timeline 410 for which no cardiac (e.g., ECG)

recordings are available can be populated with information from other sensors associated with the medical device controller. For example, the timeline 410 can be adapted to include a visual representation of patient average heart rate, patient motion or activity, or other physical parameters or environmental information for time periods for which ECG recordings were not received. The section 414 may also be represented using different visual representation than sections associated with ECG recordings. For example, as noted above, such sections 414 may be in a different color, shade, pattern, or style than sections associated with ECG recordings.

Alternatively or in additional to including generated waveforms based on sensor data, visual representations 422 of the one or more identified events (either cardiac events or non-cardiac events) can be provided on the timeline 410 at the specified time. For example, the reconstructed timeline 410 can include annotations or icons indicating when particular events occurred. In one example, an icon, such as a lightning bolt or another appropriate graphic, may be displayed adjacent to the timeline 410 to identify when a treatment was provided by the medical device. Similarly, an icon showing a lightning bolt covered by an "x" could indicate a false alarm (e.g., due to a noisy ECG signal) where the patient may have suspended or withheld treatment by pressing the response button(s).

The user interface display 400 further comprises one or more modules or sections for displaying information about the patient and/or device function for discrete times or time ranges within the total time interval. The information provided in such modules or sections can change dynamically based on input by the user (e.g., the technician or reviewer). For example, the technician or reviewer may manipulate a slider 440 to change a selected time or time range. As the position of the slider 440 is adjusted, information for the newly selected time or time range can be displayed in modules or sections of the user interface display.

In some examples, the user interface display 400 comprises a section with movement information (e.g., a patient activity section 424) for the patient based on data received from the motion sensor and/or accelerometer of the medical device controller. As noted, the information in the patient activity section 424 can dynamically change as the position of the slider 440 over the ECG timeline is adjusted by the reviewer. The patient activity section 424 comprises, for example, a list of numerical values, such as patient position or body angle values, a timer showing a time at a particular position, a timer showing time performing a particular activity, and, if the patient is in motion, a movement speed. If the patient is performing a physical activity, the patient activity section 424 can also include information about distance traveled, steps counted, or calories burned based, in part, on information received from the location identifying circuitry (e.g., GPS). In some examples, the patient activity section 424 can also include a map showing the patient's location at a particular time, or a path followed by the patient over an identified time range.

The patient activity section 424 can further comprise a visual indicia 426 of patient position, which illustrates a patient body position and/or an activity being performed by the patient. The indicia 426 can be, for example, a visual representation of a human in a particular position (e.g., standing, sitting, or lying down) and/or performing a specific physical activity (e.g., running, walking, waving arms). Finally, the patient activity section 424 may include one or more graphs 428 illustrating changes in patient movement over time. For example, the graph 428 can be a graph of patient speed throughout the time interval. Alternatively, the graph 428 can be a histogram showing a distribution of steps counted, distance traveled, or calories burned for specified time ranges.

With continued reference to FIGS. 7 and 8, the user interface display 400 further comprises sections displaying device status information (e.g., a device status section 430) for a discrete time or time range within the time interval. For example, device status information can comprise information about one or more of a system, subsystem, or component of the medical device or medical device controller. The device status information can also change dynamically based, for example, on manipulation of the slider 440 by the user. Device status information can include, for example, information about device faults, alarms, or events that occurred during the selected time or time range. In some examples, the device status section 430 of the display 400 can include a chronological list of faults or device events recorded by the medical device controller. In other examples, device operating parameters can be displayed, such as battery charge level, elapsed time since most recent flag or alarm, pulse voltage information, pulse current information, and/or electrode noise information for the specified time or time range. As shown, a graphic may be displayed in the device status section 430 to visually indicate the status of one or more devices, components, subsystems, and systems of the ambulatory medical device.

As shown in FIGS. 7 and 8, the device status section 430 can further comprise a visual representation 432 of device status at a selected time. For example, the visual indicia 432 can comprise one or more icons 434 having a first appearance when a device component is operating normally or in a satisfactory manner and a second appearance when a fault is detected for the device component. For example, as shown in FIG. 7, a visual representation of a wearable medical device (e.g., a wearable defibrillator with therapeutic electrodes, sensing electrodes, and a controller) is illustrated. Each portion of the icon in FIG. 7 has an appearance indicating that the respective component is operating normally. However, as shown in FIG. 8, the appearance of a number of the icons is changed to signify that portions of the device are not operating normally at the specified time (e.g., a device fault was identified).

A user can review device status information in the device status section 430 to help determine causes for certain identified cardiac events and/or false alarms. For example, a reviewer may review device status for a period of time immediately preceding any false alarms generated by the medical device by manipulating the slider 440. As the slider is moved forward or backward along the timeline 410, information in the device status section 430 is dynamically updated for the newly selected time or time period. By reviewing device status for times or periods preceding the false alarms, the reviewer may notice, for example, that false alarms occurred substantially immediately after the device was removed and refitted to/by the patient. In other instances, the reviewer may notice that false alarms were triggered shortly after one of the electrodes fell off or lost signal. These events may suggest, for example, that the garment and/or the electrode was not repositioned correctly or that the loss of electrode signal was not sufficiently addressed leading to the false alarm.

The user interface display can further comprise an overview section 436 providing device operating statistics for a selected time range (e.g., a 24-hour period) or for the entire time interval included in the information received from the medical device controller. For example, the overview section 436 can include time dependent data (e.g., data that can vary depending on the position of the slider 440) about one or more systems, subsystems, and/or devices of the medical system. For example, the overview section 436 may include battery information (e.g., current charge level, internal resistance value, last reported voltage, battery temperature, etc.) electrode status information (e.g., whether the electrodes are on/off), and controller status information (e.g., an operating mode of the controller, such as, active, inactive, sleep, etc., controller temperature, whether user interface is active, whether one or more self-tests performed by the controller has been completed, results of certain self-tests, etc.) For example, a time range can be selected with a drop down menu 437, as shown in FIGS. 7 and 8. The device status overview section 436 can include, for example, a list or table including a number of faults or flags identified, a number of treatment alarms, and/or a number of noise flags issued by the medical device controller. Other information fields in the overview section 436 can include, for example, a number or frequency of device false alarms, a time and duration of device faults, and/or a number of electrode falloff events recorded.

The user interface display 400 can further comprise a patient overview section 438 including values and metrics for a specified time range or for the total time interval covered by the received information. The patient overview section 438 can include, for example, information about a total duration or percentage of time with a normal sinus rhythm, as well as total noise time (e.g., total duration that a noisy ECG signal was received by the ECG electrodes), total time that the patient experiences ventricular fibrillation, a total active time for the patient, and/or a total device wear time for the specified interval. In some examples, the display 400 may further comprise a visual indication or numerical representation of a calculated overall metric of patient health and/or device status during the time interval. For example, an icon can be displayed if patient health is satisfactory and the analyzed information indicates that the patient is using the device as instructed. If the received information from the medical device indicates that the patient health is less than satisfactory or the patient is misusing the device (e.g., device drops detected, low wear time values, etc.) a different indicia or icon can be displayed.

With specific reference to FIG. 8, the slider 440 can also be adjusted to select a time range, rather than a discrete time. For example, as shown in FIG. 8, the slider 440 is shown as a rectangle shape covering a time range of one (1) second on the timeline 410. In some examples, a user may zoom out to view larger sections of the timeline 410 at one time. In the zoomed out state, the user can selected time periods longer than 1 second (e.g., from a few minutes, to a few hours, or longer) using the slider 440. When a time range is selected by the slider 440, the user interface sections or modules (e.g., the patient activity section 424 and device status section 430) can be updated to include information for the selected time range. For example, the sections 424, 430 can be populated and/or updated with information covering the selected range (e.g., including maximum and/or minimal values measured during the selected time range or average valves for the selected time range). The sections 424, 430 may also be updated to show cumulative totals for an identified time range. For example, the patient activity section 424 may be updated to show, for example, distance traveled (e.g., for a patient that is running or walking over the time range) or calories burned. The device status section 430 may be updated to show a total number of flags or alerts issued during an identified time range. Similarly, the device status section 430 may show a percentage of time with electrode fall off or other identified faults during the time range selected by the slider.

Figure 9:
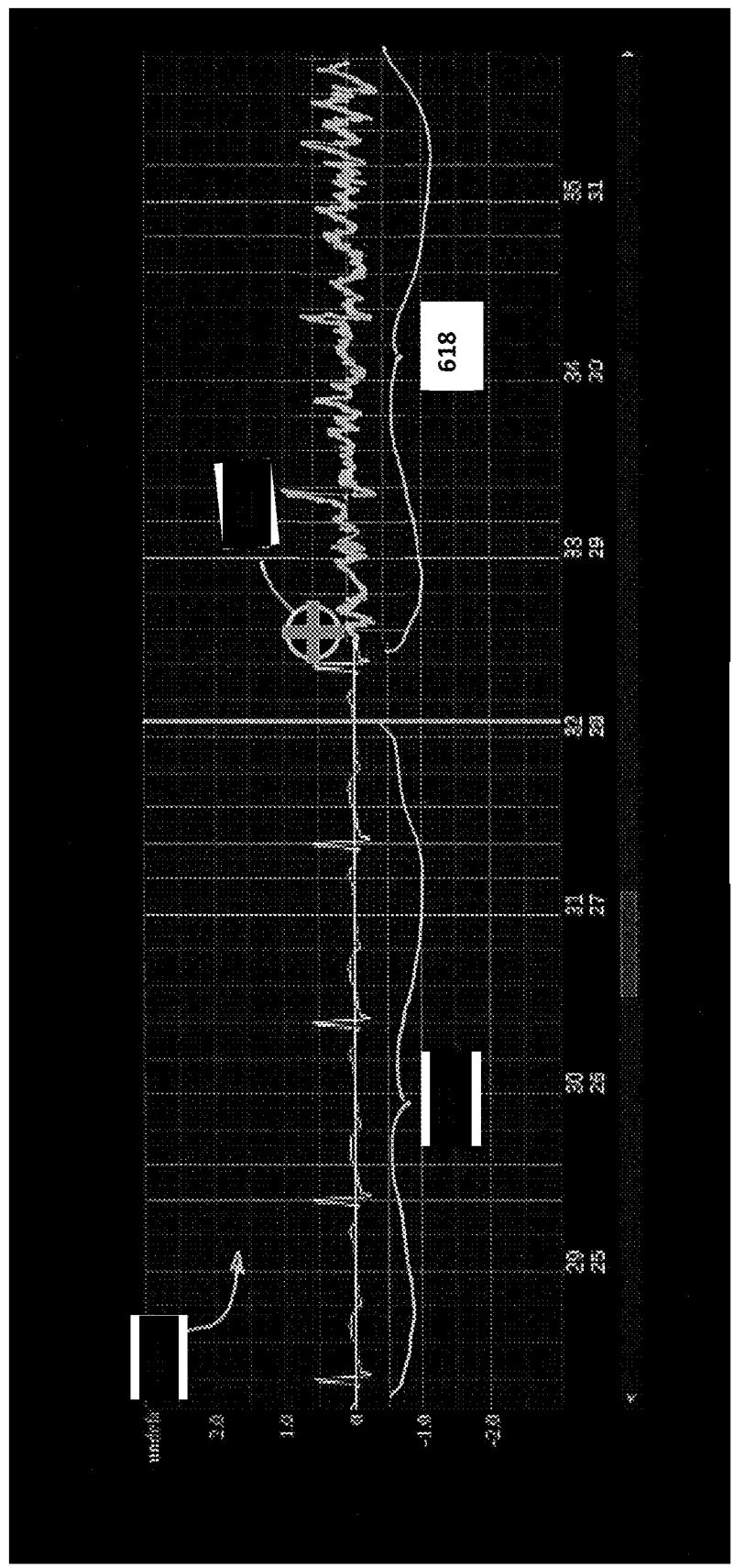
FIG. 9 depicts a portion of a user interface display including a cardiac waveform and an indication of a non-cardiac event, according to an aspect of the disclosure.

With reference to FIG. 9, another exemplary timeline 610 including sections 618 generated from ECG recordings and sections 614 generated from reconstructed ECG recordings is illustrated. The exemplary timeline 610 can be generated by the event processor as discussed herein and displayed by the user interface. The timeline 610 can include indicia for events detected or identified based on analysis of received information, such as non-cardiac data. For example, as shown in FIG. 9, an indicia 620 representative of an electrode falloff event is illustrated at a point in time between sections 614, 618. The indicia 620 can comprise a drawing or logo indicating that one or more of the ECG electrodes is off (e.g., an electrode falloff event). For example, the indicia 620 can be a circle and cross logo, as shown in FIG. 9. In other examples, the indicia 620 can be an alpha-numeric character or shape. As discussed in connection with FIGS. 7 and 8, indications of electrode falloff can also be shown in the dynamic device status section of the user interface display, such as by the visual representation of the wearable defibrillator device discussed herein.

In some examples, the medical device can identify electrode falloff by causing electrodes to provide a pulse or signal to the patient and then evaluating whether the injected signal is identified by each of the ECG electrodes. If an electrode falloff event is detected, the medical device may be configured to automatically obtain an ECG recording for a period of time immediately following the detected falloff event, as shown by section 618 in FIG. 9. However, as shown in timeline 610 the section 618 generated from the obtained ECG recording is a noisy ECG signal. Noisy ECG signals can be difficult for analysis components of the medical devices to measure and identify correctly. In some examples, a noisy ECG signal (as shown in segment 618) may cause the medical device to initiate a patient treatment sequence at times when such interventions are not required.

Such situations of unneeded treatment are referred to as false alarms or false treatment events. Advantageously, a reviewer or technician observing the timeline 610 would see that the electrode falloff indicia 620 is provided just before the noisy ECG signal was detected and recorded. Accordingly, the reviewer or technician can conclude that the electrode falloff was at least partly responsible for the recorded noisy ECG signals. In that case, the reviewer or technician may suggest troubleshooting activities for improving ECG electrode connection or adherence in order to reduce occurrence of noisy ECG signals and false alarm events. In a similar manner, indicia for other non-cardiac events could also be displayed on the timeline 610. The additional indicia can provide further information about causation of the noisy ECG and/or may provide information to assist the reviewer in determining causation for the electrode falloff. For example, if the patient was physically active just prior to electrode falloff, it may be determined or suggested that the electrode was jostled or inadvertently moved by the patient's physical activity or movement.

Exemplary Uses

In use, in the course of his or her job responsibilities, the technician or reviewer may review events or flags issued by a medical device to draw conclusions about causation and to assist in troubleshooting technical issues reported by patients and caregivers. For example, the technician or reviewer may receive a service request from a patient wearing a particular wearable therapeutic medical device. In one example scenario, a patient may report that the medical device has issued a number of false alarms (e.g., initialized treatment sequences that were suspended by the user by pressing the response button(s)). Alternatively, the reviewer may notice this issue during review of the device data. As described above, issuance of a false alarm may be a type of event for which the medical device controller can record a cardiac (e.g., ECG recording) and, in some cases, sensor data from other sources. Instead of reviewing a chronological list of ECG recordings for each identified false alarm event in an attempt to determine a cause and/or identify issues with the device, the technician or reviewer may use the technician portal 216 as described herein to efficiently and expeditiously attend to the request.

In this regard, the technician portal 216 is configured to receive and process the information from the medical device controller for a time interval including the false alarms. The received information is processed by the event processor to determine cardiac and non-cardiac events. Once the events are determined, the technician portal is configured to generate (e.g., reconstruct) a graphical representation of the events (e.g., false alarm events described in the service request, along with any other events which occurred during the specified time interval). For example, the graphical representation can include a reconstructed timeline comprising sections with visual representations of the false alarm events, visual representations of other events, such as non-cardiac events identified by the event processor, and sections for which no cardiac recordings (e.g., no ECG, heart sounds, or other cardiac-related sensor recordings) are available. Accordingly, the graphical representation or timeline provides the technician with a visual representation not only of the false alarm events, but also of device and patient status at times when no false alarms occurred.

The technician can review the information by manipulating the user interface and, for example, can manipulate the slider to adjust what information is displayed on the user interface display. For example, as previously noted, a false alarm event may be associated with a cardiac recording. Accordingly, the technician may manipulate the slider to review device and/or physiological status information for periods of time immediately preceding the false alarm events (e.g., by dragging the slider over the timeline to regions of the timeline not associated with a cardiac recording). In this manner, the technician or reviewer could determine, for example, whether the patient was performing a particular physical activity or changing position prior to each false alarm. If it is determined that the patient is moving or performing a specific activity before each false alarm, it may be evidence that the patient movement adjusted or changed contact with ECG sensors leading to the false alarm. In that case, the technician ore reviewer may suggest ways to improve electrode contact (e.g., wash the garment to improve fit) and/or suggest that the patient be provided with a smaller garment or belt to address electrode fall off. In a similar manner, the technician may review the reconstructed graphical representation to assess an amount or degree of signal noise recorded by ECG electrodes both when the false alarms occurred and at other times. If the technician or reviewer determines that the ECG electrodes generate a noisy signal for an unexpectedly high percentage of time, it may indicate that the false alarms are attributable to a noisy ECG signal. In that case, the technician or reviewer may discern that the ECG electrodes are not functioning normally and should be replaced. In other examples, review of the graphical representation may indicate that other device components contributed to the multiple false alarms. For example, review of the reconstructed timeline and other displayed information may indicate that a device parameter such as battery charge level, pulse voltage information, or pulse current information changed prior to occurrence of the false alarm events. In that case, the technician or reviewer may suggest that the patient receive training about recharging the battery at an appropriate time to address the multiple false alarms. Finally, in other examples, the technician can consider environmental factors such as time of day when the false alarms occurred (e.g., did the alarms occur while the patient was sleeping or lying down for an extended period of time), device temperature, ambient temperature, patient temperature, humidity, moisture on the patient's skin (e.g., due to sweating), patient impedance, blood pressure, or patient location to draw conclusions about medical precursors or causation for the false alarms. In any case, based on the review of the received information, the technician or reviewer can assess situations or conditions that led to the false alarm events and provide appropriate troubleshooting assistance for the patient.

Review of the information received from the medical device with the user interface can also assist the technician or data reviewer to prepare patient reports documenting the identified events. For example, the patient report can include the received information, along with additional metrics and/or numerical values for the entire time interval. In some examples, the technician or reviewer can select which images, graphs, and metrics to include in the patient report based on his or her review of the determined events displayed by the user interface. In particular, being able to review events in context of other physiological and device status information may assist the technician or reviewer to select types of information to include in the patient report, which may be of particular interest to the patient or physician.

Patient Monitoring Device User Interface

Figure 10:
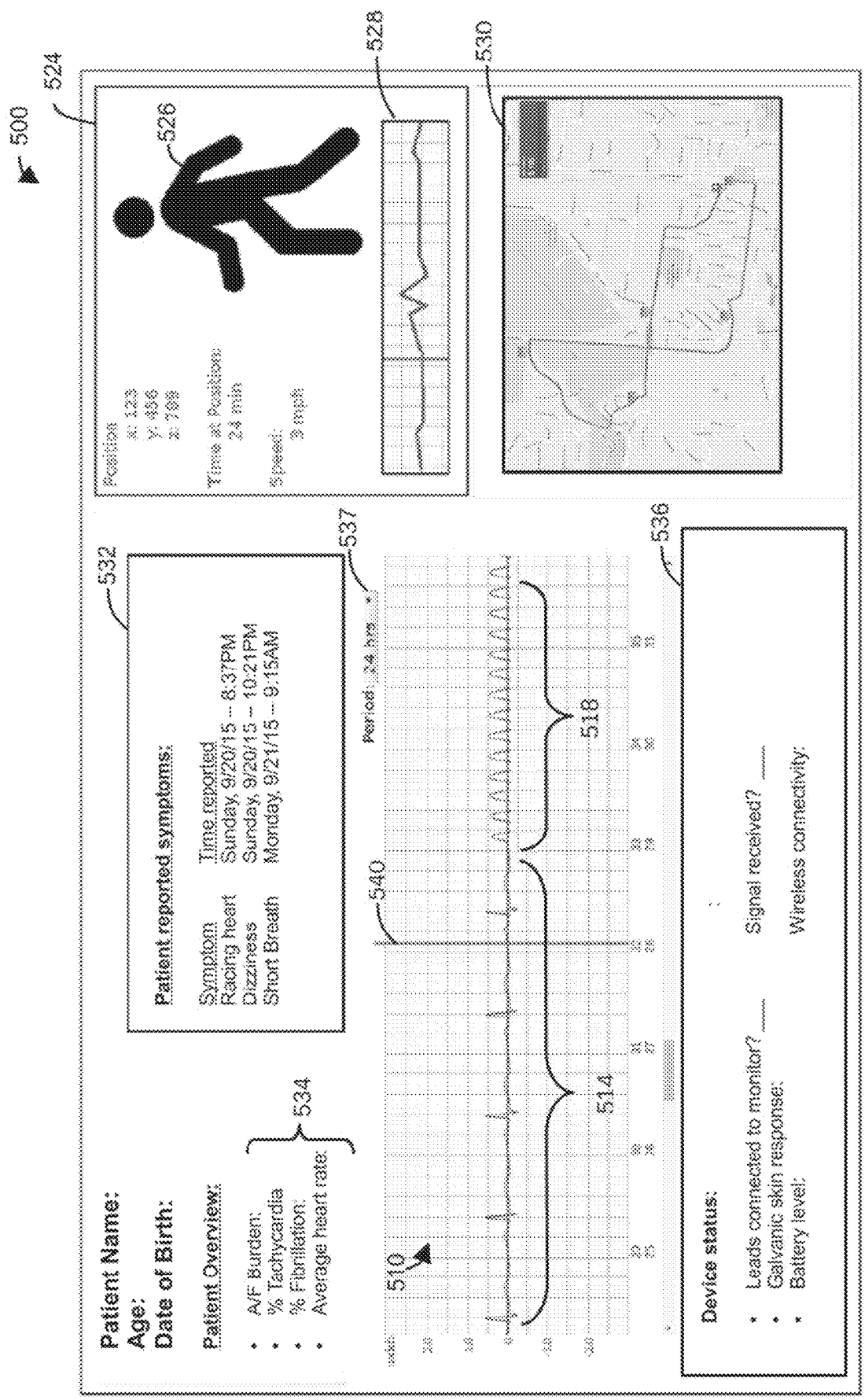
FIG. 10 depicts a user interface display for reviewing information received from a patient monitoring device, according to an aspect of the disclosure.

With reference to FIG. 10, an example user interface display 500 for reviewing information received from a patient monitoring device (such as an MCT/CEM device) is illustrated. The user interface display 500 comprises a generated reconstructed timeline 510, similar to the timeline 410 (shown in FIGS. 7 and 8). The timeline 510 comprises sections 518 generated from received cardiac recordings and sections 514 generated for periods of time for which cardiac recordings were not recorded or received. As in previously described examples, the sections 518 based on cardiac recordings can have a first appearance (e.g., first color, shade, pattern, or style) and the sections 514 generated without cardiac recordings can have a second appearance (e.g., second color, shade, pattern, or style) to assist reviewers in differentiating between the sections 514, 518. In general, the reviewer should be able to easily appreciate which sections of the timeline 510 are based on cardiac recordings (ECG or heart sounds recordings) and which sections are not cardiac recordings (e.g., such as based on estimated, baseline ECG or heart sounds values).

As was the case with the patient activity section 424 and device status section 430 (shown in FIGS. 7 and 8), the user interface display 500 can further comprise sections or modules including information for discrete times or time ranges within the total time interval. The reviewer can select the time interval using, for example, the slider 540. As the user adjusts the position of the slider 540, the sections or modules are dynamically updated to reflect the newly selected time or time range.

In some examples, the user interface includes a patient activity section 524, similar to the patient activity section 424 (shown in FIGS. 7 and 8). The patient activity section 524 comprises a list of numerical values, such as patient position or body angle values, a timer showing a time at a particular position, a timer showing time performing a particular activity, and, if the patient is in motion, a movement speed. If the patient is performing a physical activity, the patient activity section 524 can also include information about distance traveled, steps counted, or calories burned based, in part, on information received from the location identifying circuitry (e.g., GPS). In some examples, the display 500 can further comprise a map 530 illustrating patient location over a period of time. For example, the map 530 may display location information for the patient for a specific time period (e.g., 60 minutes preceding time indicated by the slider 540).

As in previously described examples, the patient activity section 524 can further comprise a visual indicia 526 of patient position, which illustrates a patient body position and/or an activity being performed by the patient. The indicia 526 can be, for example, a visual representation of a human in a particular position (e.g., standing, sitting, or lying down) and/or performing a specific physical activity (e.g., running, walking, waving arms). The patient activity section 524 may further comprise one or more graphs 528 illustrating changes in patient movement over time. For example, the graph 528 can be a graph of patient speed throughout the time interval. Alternatively, the graph 528 can be a histogram showing a distribution of steps counted, distance traveled, or calories burned for specified time ranges.

In some examples, the user interface further comprises a section 532 displaying information manually entered by the patient. For example, the patient can manually enter symptom information describing symptoms which often relate to cardiac events. In some instances, the patient monitor may provide survey questions to the patient after a cardiac event is detected to assess whether the cardiac event resulted in symptoms for the patient. In other examples, the patient may report experiencing symptoms when they occur and without being prompted by the patient monitor. The section 532 may comprise a list of patient reported symptoms and times that the symptoms were reported. In some examples, the section 532 can update dynamically to show the reported symptoms closest to the time selected by the slider 540. In other examples, the section 532 may be configured to list all symptoms reported by the patient during a time interval.

In some examples, the user interface display 500 can further comprise a section 536 with information about device status. As shown in FIG. 10, the section 536 can include information about electrode status, such as whether electrodes are attached to the patient monitor and whether an ECG signal is being received. The section may also include information about galvanic skin response, which can be used to determine if electrodes are attached to the patient's skin in the recommended manner. The section 536 can also include information about device battery level and about whether the device had wireless connectivity for transmitting data at the time indicated by the slider 540.

In some examples, the user interface display 500 can further comprise a section 534 with an overview of selected statistics for a time interval. For example, the patient overview section can include information related to one or more of the following: A/F burden, percentage of time with tachycardia and/or fibrillation, and average heart rate. The overview section can include statistics for the entire treatment interval or for a selected time period. For example, the user may select a specific time period (e.g., 12 hours, 24 hours, 1 week) using the drop down menu 537 shown in FIG. 10. The patient overview section 534 can be updated to reflect statistics for the selected time period.

In use, a data reviewer may use the user interface to review information collected by a patient monitor. As described herein, such patient monitors are generally worn for a predetermined period (e.g., about 30 days). The reviewer may be responsible for preparing patient reports on a periodic basis (e.g., daily or weekly), as well as a final patient report at the end of the monitoring period. In order to prepare a patient report, the reviewer uses the user interface to examine collected information. For example, the reviewer may begin by examining portions of the timeline generated from ECG records. As described herein, the sections 518 of the timeline based on received cardiac records can have specific appearance (e.g., color, style, or pattern) to differentiate them from sections 514 not based on received cardiac records. For example, the reviewer may scroll through the timeline to center an ECG recording in the viewing window shown on the user interface display. The reviewer may examine the ECG recording to confirm that an event, such as an arrhythmia or tachycardia, is present in the recorded ECG and, if an arrhythmia is present, may obtain a screen capture image of the ECG trace for the identified arrhythmia to include in the patient report.

After reviewing the ECG traces based on cardiac records, the reviewer can manipulate the slider 540 to review information for the discrete time that the cardiac event occurred. As described above, the other modules or sections of the user interface display are dynamically updated to show information for the discrete time or time range identified by the slider. For example, the user can review information in the patient activity section to determine patient's position and/or activity during the cardiac event. The user can also adjust the position of the slider to determine the patient's activity level and/or position at times preceding the cardiac event (e.g., 1 minute before the event, 5-30 minutes before the event, or even hours before the event). The patient activity information for times preceding the event may help the reviewer to draw conclusions about causation of the cardiac event. For example, the reviewer may consider patient sleeping position (e.g., patient body position during sleep) to identify whether certain sleeping positions were more likely to cause cardiac events. The reviewer can review periods of time preceding other identified cardiac events to determine whether the patient was in a similar body position and/or activity level prior to other identified cardiac events. In a similar manner, the reviewer may examine portions of the timeline with large gaps between identified events to see whether certain patient activities and/or body positions may have reduced occurrence of cardiac events. For example, the reviewer may see that the patient was less likely to experience a cardiac event when sleeping in a particular position. In other examples, non-cardiac physiological data for time periods preceding cardiac events may be reviewed. For example, the reviewer may notice that the patient experienced difficulty breathing or other ventilation issues prior to cardiac events. Such information may be used by the reviewer or the patient's doctor about causation for certain identified events.

In some examples, the reviewer may include portions of the reconstructed timeline in the patient report. For example, the reviewer may include a timeline showing onset of an identified cardiac event. The timeline may include annotations shown patient activity and/or non-cardiac physiological data for the time immediately preceding onset of the cardiac event, to help the physician to understand patient activity levels and other parameters that may have contributed to onset of the cardiac event. The reviewer can include such information in patient reports. For example, the patient report can include patient activity levels for times of particular interest. The reviewing physician may be interested in discussing such activity result with the patient.

The reviewer may also review patient reported symptom information for periods of time preceding or following cardiac events. For example, in some instances, patients may self-report experiencing symptoms using the patient monitoring device, in the manner described herein. The patient reported symptom information for discrete times or time ranges can be displayed in the patient information module described above. Similarly, patient symptom information can be shown on or adjacent to the generated timeline with icons or indicators. The reviewer can review when patient reported symptoms occur to draw conclusions about whether the symptoms relate to onset of a cardiac event or to other causes. For example, the reviewer may consider whether some symptoms are related to patient activity level, environmental factors, or other causes rather than to onset of a cardiac event. Similarly, the reviewer may consider patient reported symptom information for periods of time immediately following cardiac events to determine whether the patient is seeking appropriate care for certain events or even whether the patient is able to perceive that such events occur (e.g., did the patient report experiencing symptoms at the same time as a cardiac event shown in the recorded ECG). The information based on review of patient symptom data can be provided to the physician or caregiver in the patient report. For example, the reviewer may create images or screen captures showing patient response data in combination with the ECG traces to show the physician relationships between patient symptom information and ECG data that may be of interest or concern.

The embodiments and aspects of the disclosure have been described with reference to various examples. Modifications and alterations will occur to others upon reading and understanding the foregoing examples. Accordingly, the foregoing examples are not to be construed as limiting the disclosure.

What is claimed is:

1. A system for providing a graphical representation of information comprising:
   a wearable defibrillator comprising:
      a garment configured to be worn on a torso of a patient;
      a shock generator supported by the garment and configured to generate an electrical therapeutic shock;
      one or more therapy electrodes configured to provide the shock from the shock generator to the patient;
      one or more ECG sensors configured to detect an ECG signal of the patient;
      one or more motion sensors configured to detect one or more motion signals, the one or more motion sensors comprising a single axis accelerometer, a multi-axis accelerometer, or a gyroscope;
      a memory in communication with the sensors, the memory configured to store the detected ECG and motion signals of the patient;
      at least one defibrillator processor in communication with the shock generator, electrodes, sensors and memory, configured to:
         cause the shock generator to provide the electrical therapeutic shock to the patient in response to certain detected cardiac events;
         process the ECG signals from the one or more ECG sensors to detect cardiac events in the ECG signals;
         wirelessly transmit a plurality of ECG recordings generated from the ECG signals for time intervals including the cardiac events; and
         wirelessly transmit motion data generated from the one or more motion signals for the time intervals including the cardiac events and for time intervals without cardiac events;
   at least one processor remote from and in wireless communication with the wearable defibrillator configured to process information received from the wearable defibrillator; and
   a user interface device operably connected to the at least one processor, wherein the at least one processor is configured to:
      receive the plurality of ECG recordings for the time intervals including the cardiac events,
      identify time periods between the plurality of ECG recordings for which ECG recordings are not available,
      process the motion data for the time intervals including the cardiac events and for the time periods between the plurality of ECG recordings to identify one or more motion events occurring during the time intervals including the cardiac events and during the time periods between the plurality of ECG recordings, wherein the motion events are related to at least one of movement or physical activity of the patient identified based on the motion data generated by the one or more motion sensors,
      determine at least one of times of occurrences and time periods associated with the cardiac events,
      determine at least one of times of occurrences and time periods associated with the one or more motion events, and
      generate, for display on the user interface device, a graphical representation of the processed information for the identified events, the graphical representation comprising:
         a time-dependent ECG waveform generated from the plurality of ECG recordings;
         at least one non-ECG motion graphical event indicator for the identified one or more motion events occurring during time periods between the plurality of ECG recordings, the at least one non-ECG motion graphical event indicator indicating (i) the time of occurrence for the motion event and (ii) that the identified one or more motion events occurred during one of the time periods between the plurality of ECG recordings;
         at least one ECG motion graphical event indicator for the identified one or more motion events occurring during the time intervals including the cardiac events, the at least one ECG motion graphical event indicator indicating (i) the time of occurrence for the identified one or more motion events and (ii) that the identified one or more motion events occurred during the time intervals including the cardiac events; and
         at least one visual indication generated based on the motion data, the at least one visual indication indicating at least one of (i) a body position of the patient during a selected discrete time or (ii) a type of physical activity being performed by the patient during the selected discrete time; and
   causing the user interface device to display the graphical representation.

2. The system of claim 1, wherein the cardiac events comprise one or more of: a patient-initiated event, a remotely triggered event, a device-initiated event, and a cardiac arrhythmia event, and wherein the graphical representation comprises an indication of event type.

3. The system of claim 1, wherein the cardiac events comprise a false alarm to the patient and the graphical representation provides a reviewer with an ability to determine a potential cause of the false alarm, and wherein the at least one motion graphical event indicator provides the reviewer with an ability to review information about the one or more motion events with respect to the at least one of the time of occurrence and the time period associated with the false alarm to determine the potential cause of the false alarm.

4. The system of claim 1, wherein the graphical representation provides a reviewer with an ability to review information about one or more of a system, subsystem, and a component of the wearable defibrillator during analysis of the cardiac events.

5. The system of claim 4, wherein the information about the one or more of the system, subsystem, and the component of the wearable defibrillator includes battery information, electrode status information, and controller status information.

6. The system of claim 1, wherein the one or more motion events further comprise one or more of a physiological event, a device-initiated event, and an event related to a patient location.

7. The system of claim 6, wherein the at least one non-ECG motion graphical event indicator and/or the at least one ECG motion graphical event indicator for the identified one or more motion events further comprises an indication representative of a device-initiated event comprising one or more of: a number of device faults over the time intervals, a time and duration of device faults over the time intervals, an amount of time since the most recent fault, a device battery level, a number of electrode fall off events over the time intervals, pulse voltage information, pulse current information, a number of abnormal device shutdowns over the time intervals, diagnostic test results, and/or electrode noise information.

8. The system of claim 7, wherein the at least one non-ECG motion graphical event indicator and/or the at least one ECG motion graphical event indicator comprises an icon, and wherein at least a portion of the icon has a first appearance when there are no faults over the time intervals and at least a portion of the icon has a second appearance when there are one or more faults over the time intervals.

9. The system of claim 1, wherein the at least one non-ECG motion graphical event indicator and/or the at least one ECG motion graphical event indicator for the identified one or more motion events further comprises information relating to one or more of: patient body position, patient body angle, time performing the physical activity, movement speed, and/or movement rate.

10. The system of claim 1, wherein the at least one visual indication comprises a visual indicator that the patient is laying down, sitting, standing, walking, or running.

11. The system of claim 1, wherein the graphical representation of the information further comprises at least one overall metric calculated from the received ECG recordings and motion data from the wearable defibrillator, the overall metric comprising one or more of: a number of treatments administered by the wearable defibrillator over the time intervals, an amount of time with normal cardiac activity over the time intervals, an amount of time with abnormal cardiac activity over the time intervals, an amount of time in which the received information includes signal noise above a threshold amount, a patient active time over the time intervals, a device wear time over the time intervals, a number of identified device faults over the time intervals, and/or a number of identified signal noise events over the time intervals.

12. The system of claim 1, wherein the graphical representation further comprises at least one graphical indication for distinguishing between the time intervals including the cardiac events and the time intervals without cardiac events between the plurality of ECG recordings.

13. The system of claim 1, wherein the user interface device is further configured to update the at least one visual indication generated based on the motion data based on a received selection of another discrete time.

14. The system of claim 1, wherein the at least one wearable defibrillator is further configured to wirelessly transmit information comprising a type of cardiac event and cardiac event outcome for the plurality of ECG recordings generated from the ECG signals.

15. The system of claim 14, wherein the information about cardiac event outcome for the plurality of ECG recordings comprises an indication that treatment was provided or that the cardiac event was a false alarm,
wherein the at least one remote processor is further configured to: (i) process the motion data for time periods of ECG recordings comprising the false alarm to identify motion events occurring simultaneous with the false alarm, and (ii) generate an instruction to a system user for display on the user interface device to review the identified motion events occurring simultaneous with the false alarm to determine whether patient movement contributed to the false alarm.

16. The system of claim 14, wherein the wirelessly transmitted information from the at least one wearable defibrillator comprises information identifying ECG recordings comprising electrode fall off events that did not result in providing treatment to the patient, and
wherein the at least one remote processor is configured to: (i) process the motion data for time periods of ECG recordings comprising the electrode fall off events to identify motion events occurring simultaneous with the electrode fall off events, and (ii) generate an instruction to a system user for display on the user interface device to review the identified motion events occurring simultaneous with the electrode fall off events to determine whether patient movement contributed to the electrode fall off event.

17. A system for providing dynamic viewing of information, the system comprising:
a wearable defibrillator comprising:
a garment configured to be worn on a torso of a patient;
a shock generator supported by the garment and configured to generate an electrical therapeutic shock;
one or more therapy electrodes configured to provide the shock from the shock generator to the patient;
one or more ECG sensors configured to detect an ECG signal of the patient;
one or more motion sensors configured to detect one or more motion signals, the one or more motion sensors comprising a single axis accelerometer, a multi-axis accelerometer, or a gyroscope;
a memory in communication with the sensors, the memory configured to store the detected ECG and motion signals of the patient; and at least one defibrillator processor in communication with the shock generator, electrodes, sensors, and memory, configured to:
  process the ECG signals from the one or more ECG sensors to detect cardiac events in the ECG signals;
  wirelessly transmit a plurality of ECG recordings generated from the ECG signals for time intervals including the cardiac events; and
  wirelessly transmit motion data generated from the detected motion signals for the time intervals including the cardiac events and for time intervals without cardiac events;
at least one processor remote from and in wireless communication with the wearable defibrillator configured to process information received from the wearable defibrillator, wherein the at least one processor is configured to:
  receive the plurality of ECG recordings for the time intervals including the cardiac events,
  identify time periods between the plurality of ECG recordings for which ECG recordings are not available,
  process the motion data for the time intervals including the cardiac events and for the time periods between the plurality of ECG recordings to identify one or more motion events occurring during the time intervals including the cardiac events and during the time periods between the plurality of ECG recordings, wherein the one or more motion events are related to movement or physical activity of the patient identified based on the motion data generated by the one or more motion sensors, and
  generate, for display on the user interface device, a graphical representation of the plurality of ECG recordings and the motion data, the graphical representation comprising:
    a continuous timeline comprising:
      (a) first portions based on both the plurality of ECG recordings and the motion data, the first portions comprising a time-dependent ECG waveform generated from the plurality of ECG recordings and at least one ECG motion graphical event indicator for the identified one or more motion events occurring during the time intervals including the cardiac events, the at least one ECG motion graphical event indicator indicating (i) the time of occurrence for the identified one or more motion events and (ii) that the identified one or more motion events occurred during the time intervals including the cardiac events, and
      (b) second portions for time periods occurring between the plurality of ECG recordings based only on the motion data, the second portions of the continuous timeline comprising timeline segments connecting the time-dependent ECG waveforms of the first portions and at least one non-ECG motion graphical event indicator for the one or more identified motion events occurring during the time periods between the plurality of ECG recordings, the at least one non-ECG motion graphical event indicator indicating (i) the time of occurrence for the identified one or more motion events and (ii) that the identified motion event occurred during the time periods between the plurality of ECG recordings; and
    at least one visual indication generated based on the motion data for time periods between the plurality of ECG recordings, the at least one visual indication indicating at least one of (i) a body position of the patient during a selected discrete time or (ii) a type of physical activity being performed by the patient during the selected discrete time; and
  at least one user interface device operably connected to the at least one processor, the at least one user interface device being configured to:
    display the graphical representation of the processed information, and
    display a slider configured to be manipulated along the continuous timeline by a user, the slider being configured to select the discrete time within the time intervals for the at least one visual indication,
  wherein manipulation of the slider along the continuous timeline changes the selected discrete time, thereby causing the at least one user interface device to display an updated graphic representation comprising an updated at least one visual indication generated based on the motion data for the discrete time selected by the slider.

18. The system of claim 17, wherein the at least one visual indication further comprises an indication of one or more of: patient physiological status for the selected discrete time, and/or an indication of device status for the selected discrete time.

* * * * *